United States Patent
Tsang et al.

(10) Patent No.: US 11,000,425 B2
(45) Date of Patent: *May 11, 2021

(54) ARTICLE WITH ELASTIC DISTRIBUTION AND SYSTEM AND METHOD FOR MAKING SAME

(71) Applicant: DSG TECHNOLOGY HOLDINGS LTD., Kwai Chung (HK)

(72) Inventors: Patrick King Yu Tsang, Tuen Mun (HK); Anne Smid, Wolvega (NL); Andrew C. Wright, Derbyshire (GB); Eugenio Varona, Marietta, GA (US)

(73) Assignee: DSG Technology Holdings Ltd., Kwai Chung (HK)

( * ) Notice: Subject to any disclaimer, the term of this patent is extended or adjusted under 35 U.S.C. 154(b) by 309 days.

This patent is subject to a terminal disclaimer.

(21) Appl. No.: 16/006,700

(22) Filed: Jun. 12, 2018

(65) Prior Publication Data

US 2018/0353351 A1     Dec. 13, 2018

Related U.S. Application Data

(63) Continuation of application No. 14/946,528, filed on Nov. 19, 2015, now Pat. No. 10,045,887, which is a
(Continued)

(51) Int. Cl.
    *A61F 13/49*       (2006.01)
    *A61F 13/14*       (2006.01)
(Continued)

(52) U.S. Cl.
CPC .. *A61F 13/49019* (2013.01); *A61F 13/15593* (2013.01); *A61F 13/15609* (2013.01);
(Continued)

(58) Field of Classification Search
CPC ............. A61F 13/15609; A61F 13/496; B32B 37/144; B32B 2555/02; Y10T 156/1054; Y10T 156/1056
See application file for complete search history.

(56) References Cited

U.S. PATENT DOCUMENTS 4,284,454 A    8/1981   Joa
4,323,070 A    4/1982   Ternstroem et al.
(Continued)

FOREIGN PATENT DOCUMENTS

EP          0405575 A1     1/1991
EP          0623331 A2    11/1994
(Continued)

OTHER PUBLICATIONS

International Search Report dated Aug. 8, 2018, during the prosecution of International Application No. PCT/US2018/019296. [5 pages].
(Continued)

*Primary Examiner* — Mark A Osele
*Assistant Examiner* — Christopher C Caillouet
(74) *Attorney, Agent, or Firm* — Alberto Q. Amatong, Jr.; Amatong McCoy LLC

(57) ABSTRACT

A method is described for making an elasticized absorbent article having a waist opening and a pair of leg openings. First, multiple distributions of elastics are applied on a moving material sheet to form a moving web of an elastic composite. Then, each of a core section and a second material sheet is periodically applied onto the moving web to define a finished web of discrete elastic composite bodies. In subsequent steps, discrete absorbent pants articles are shaped from the finished web.

24 Claims, 15 Drawing Sheets

Related U.S. Application Data continuation of application No. 13/200,100, filed on Sep. 16, 2011, now Pat. No. 9,205,003.

(60) Provisional application No. 61/403,488, filed on Sep. 16, 2010.

(51) Int. Cl.
  *A61F 13/15* (2006.01)
  *B32B 37/14* (2006.01)
  *A61F 13/496* (2006.01)

(52) U.S. Cl.
  CPC .. *A61F 13/15707* (2013.01); *A61F 13/15723* (2013.01); *A61F 13/15747* (2013.01); *A61F 13/496* (2013.01); *A61F 13/49011* (2013.01); *A61F 13/49014* (2013.01); *B32B 37/144* (2013.01); *A61F 2013/15715* (2013.01); *A61F 2013/49038* (2013.01); *A61F 2013/49092* (2013.01); *B32B 2555/02* (2013.01)

(56) References Cited

U.S. PATENT DOCUMENTS

| | | | |
|---|---|---|---|
| 4,801,345 | A | 1/1989 | Dussaud et al. |
| 5,055,103 | A | 10/1991 | Nomura et al. |
| 5,092,861 | A | 3/1992 | Nomura et al. |
| 5,147,487 | A | 9/1992 | Nomura et al. |
| 5,213,645 | A | 5/1993 | Nomura et al. |
| 5,340,424 | A | 8/1994 | Matsushita |
| 5,342,341 | A | 8/1994 | Igaue et al. |
| 5,413,654 | A | 5/1995 | Igaue et al. |
| 5,440,764 | A | 8/1995 | Matsushita |
| 5,576,091 | A | 11/1996 | Lajaczkowski et al. |
| 5,634,917 | A | 6/1997 | Fujioka et al. |
| 5,735,839 | A | 4/1998 | Kawaguchi et al. |
| 5,766,411 | A | 6/1998 | Wilson |
| 5,779,689 | A | 7/1998 | Pfeifer et al. |
| 5,858,151 | A | 1/1999 | Igaue et al. |
| RE37,154 | E | 5/2001 | Nomura et al. |
| 6,364,863 | B1 | 4/2002 | Yamamoto et al. |
| 6,391,013 | B1 | 5/2002 | Suzuki et al. |
| 6,520,945 | B1 | 2/2003 | Hansson |
| 6,554,815 | B1 | 4/2003 | Umebayashi |
| 6,623,468 | B2 | 9/2003 | Shimoe |
| 6,736,923 | B1 | 5/2004 | Franzmann et al. |
| 6,905,565 | B2 | 6/2005 | Shimoe |
| 6,913,664 | B2 | 7/2005 | Umebayashi et al. |
| 7,008,497 | B2 | 3/2006 | Nakakado et al. |
| 7,037,301 | B1 | 5/2006 | Ohashi et al. |
| 7,087,044 | B2 | 8/2006 | Ohnishi |
| 7,097,725 | B2 | 8/2006 | Yoneoka et al. |
| 7,459,050 | B2 | 12/2008 | Karlsson et al. |
| 7,638,014 | B2 | 12/2009 | Coose et al. |
| 7,708,849 | B2 | 5/2010 | Mccabe |
| 7,727,214 | B2 | 6/2010 | Torigoshi et al. |
| 8,075,722 | B2 | 12/2011 | Takahashi et al. |
| 8,215,362 | B2 | 7/2012 | Yamamoto |
| 8,235,961 | B2 | 8/2012 | Nakaoka et al. |
| 8,382,735 | B2 | 2/2013 | Torigoshi et al. |
| 8,545,654 | B2 | 10/2013 | Lakso et al. |
| 2002/0049421 | A1 | 4/2002 | Hayase et al. |
| 2004/0108043 | A1 | 6/2004 | Otsubo |
| 2005/0010188 | A1 | 1/2005 | Glaug et al. |
| 2006/0064069 | A1 | 3/2006 | Rajala et al. |
| 2008/0033387 | A1 | 2/2008 | Wastlund-Karlsson et al. |
| 2009/0320993 | A1 | 12/2009 | Yamamoto |
| 2010/0076394 | A1 | 3/2010 | Hayase et al. |
| 2010/0078119 | A1 | 4/2010 | Yamamoto |
| 2010/0191212 | A1 | 7/2010 | Torigoshi et al. |

FOREIGN PATENT DOCUMENTS

| | | |
|---|---|---|
| EP | 1240881 A2 | 9/2002 |
| EP | 1621168 A1 | 2/2006 |
| JP | H06296643 A | 10/1994 |
| JP | H07284509 A | 10/1995 |
| JP | H08132576 A | 5/1996 |
| JP | H11140706 A | 5/1999 |
| JP | 2001240299 A | 9/2001 |
| JP | 2002345883 A | 12/2002 |
| JP | 2006087564 A | 4/2006 |
| JP | 2008131968 A | 6/2008 |
| JP | 2009153841 A | 7/2009 |
| JP | 2010115282 A | 5/2010 |
| WO | 2007133146 A1 | 11/2007 |

OTHER PUBLICATIONS

Written Opinion dated Aug. 8, 2018, during the prosecution of International Application No. PCT/US2018/019296. [8 pages].
First Examination Report issued in corresponding New Zealand Patent Application No. 609001, dated Jan. 15, 2014; 2 pages.
First Examination Report issued in corresponding New Zealand Patent Application No. 708577, dated Jun. 11, 2015; 3 pages.
First Office Action issued in corresponding Japanese Patent Application No. 250438, dated Jun. 3, 2015, including English Translation; 8 pages.
International Search Report and Written Opinion dated Jan. 30, 2012 (issued in PCT Application No. PCT/US11/01607).
Machine translation of Abstract of JP H07284509 a from Espacenet (http://worldwide.espacenet.com); Figures are same as cited reference U.S. Pat. No. 5,055,103 (Nomura, et al.); 2 pages.
Machine translation of Abstract of JP H08132576 from Espacenet (http://worldwide.espacenet.com); 2 pages.
Second Examination Report issued in corresponding New Zealand Patent Application No. 708577, dated Dec. 1, 2016; [3 pages].
Supplementary EP Search Report, issued in EP Application No. 11825570.2 dated Nov. 30, 2017 [10 pages].
Third Examination Report issued in corresponding New Zealand Patent Application No. 708577, dated Jan. 19, 2017.

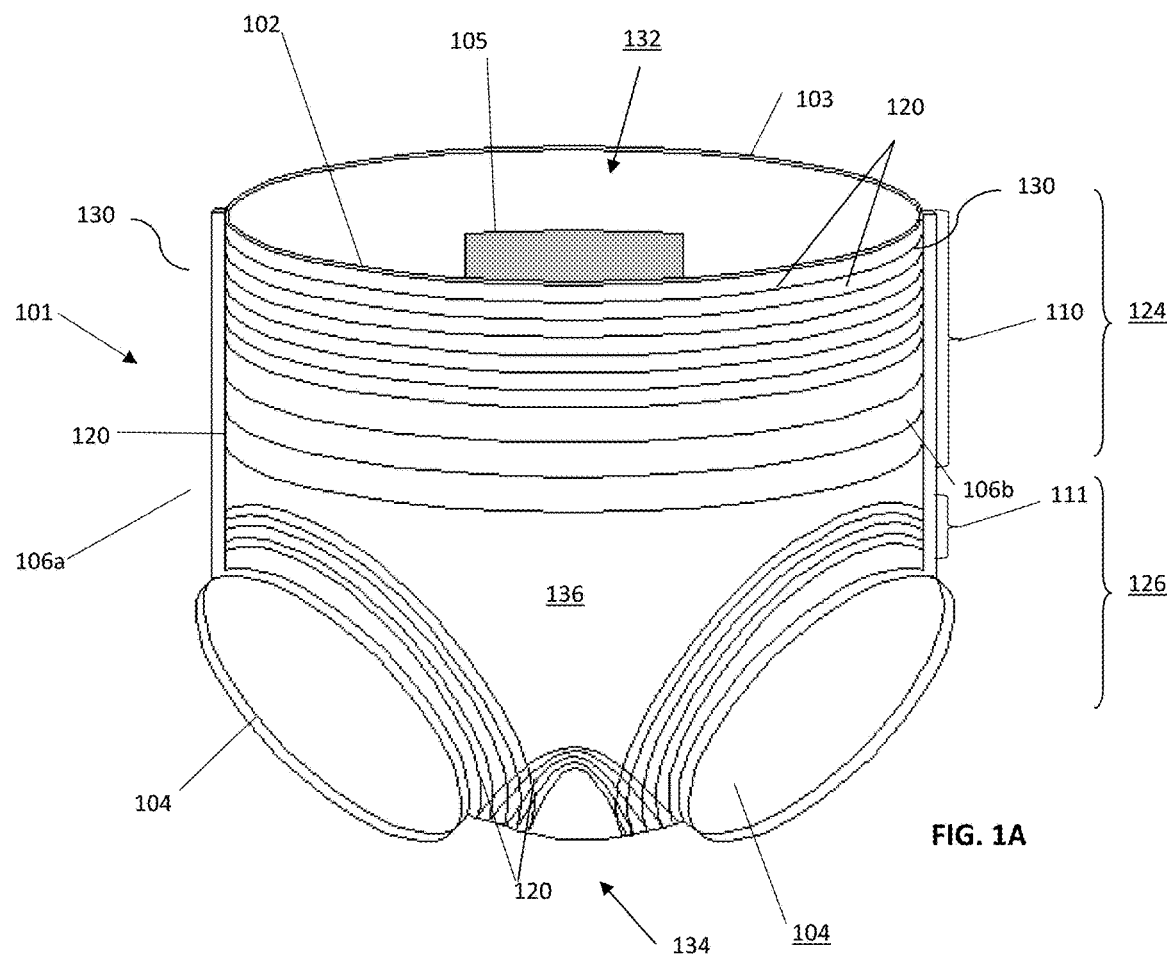
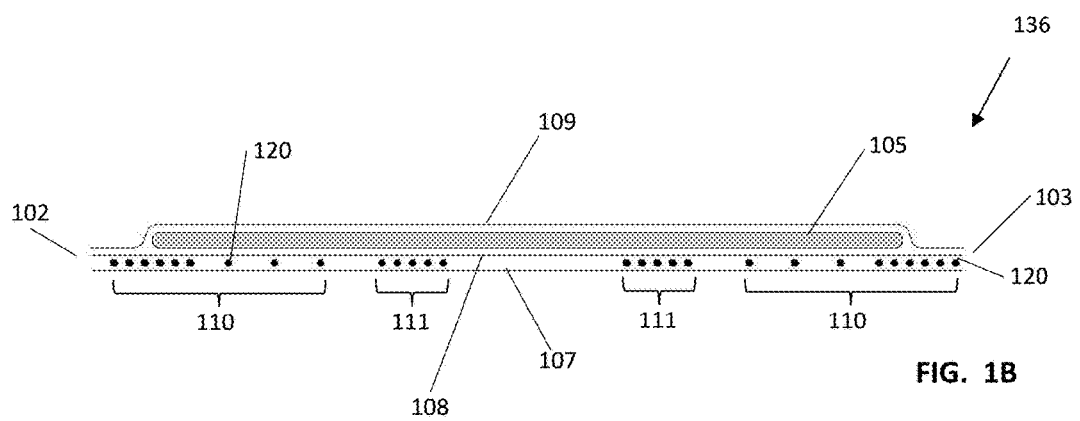

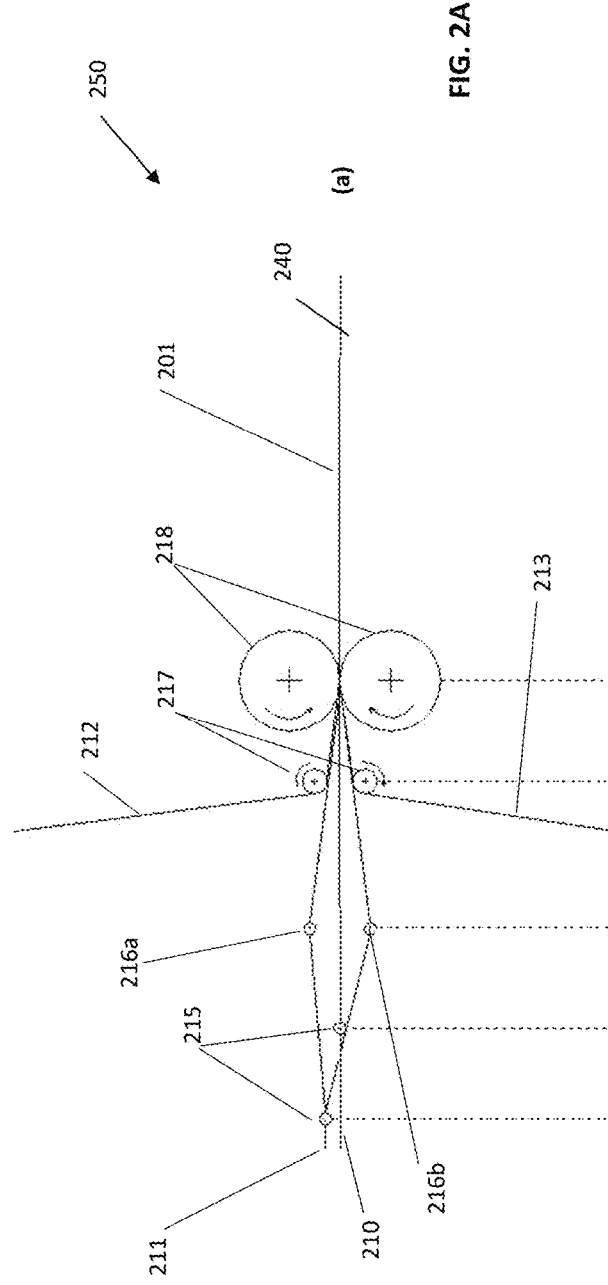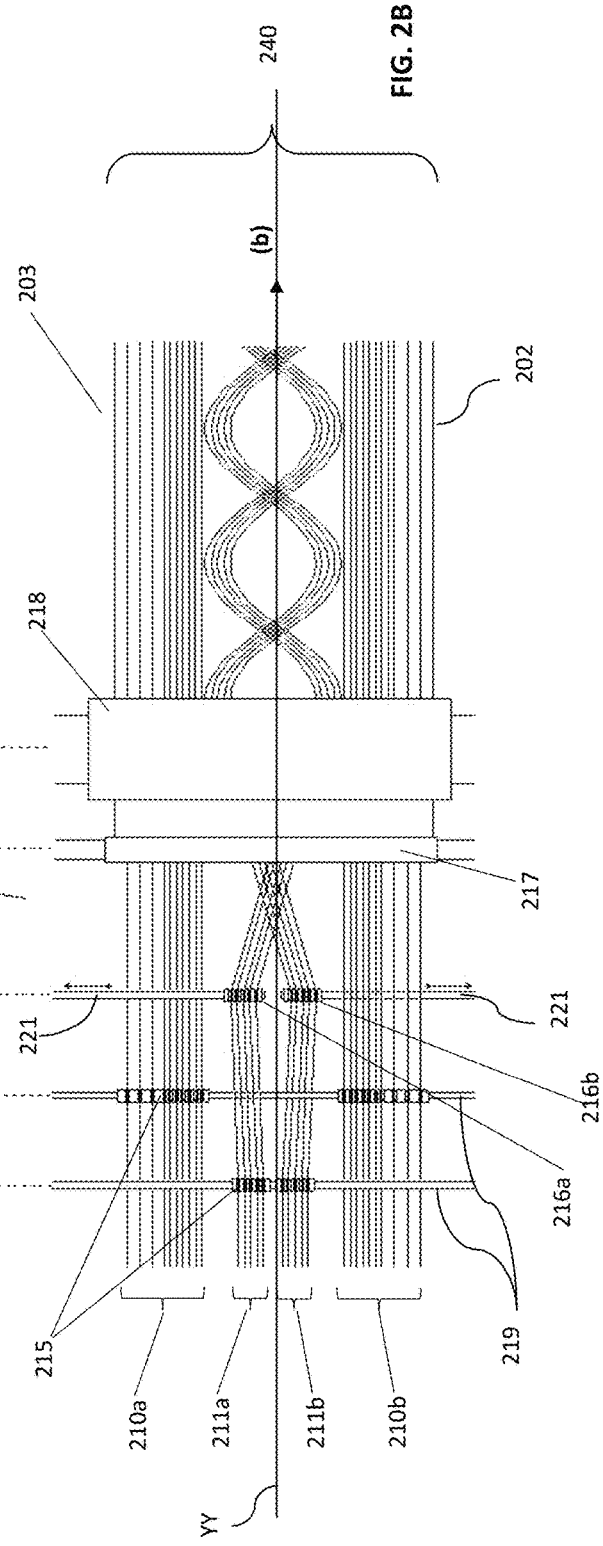
FIG. 2A
FIG. 2B

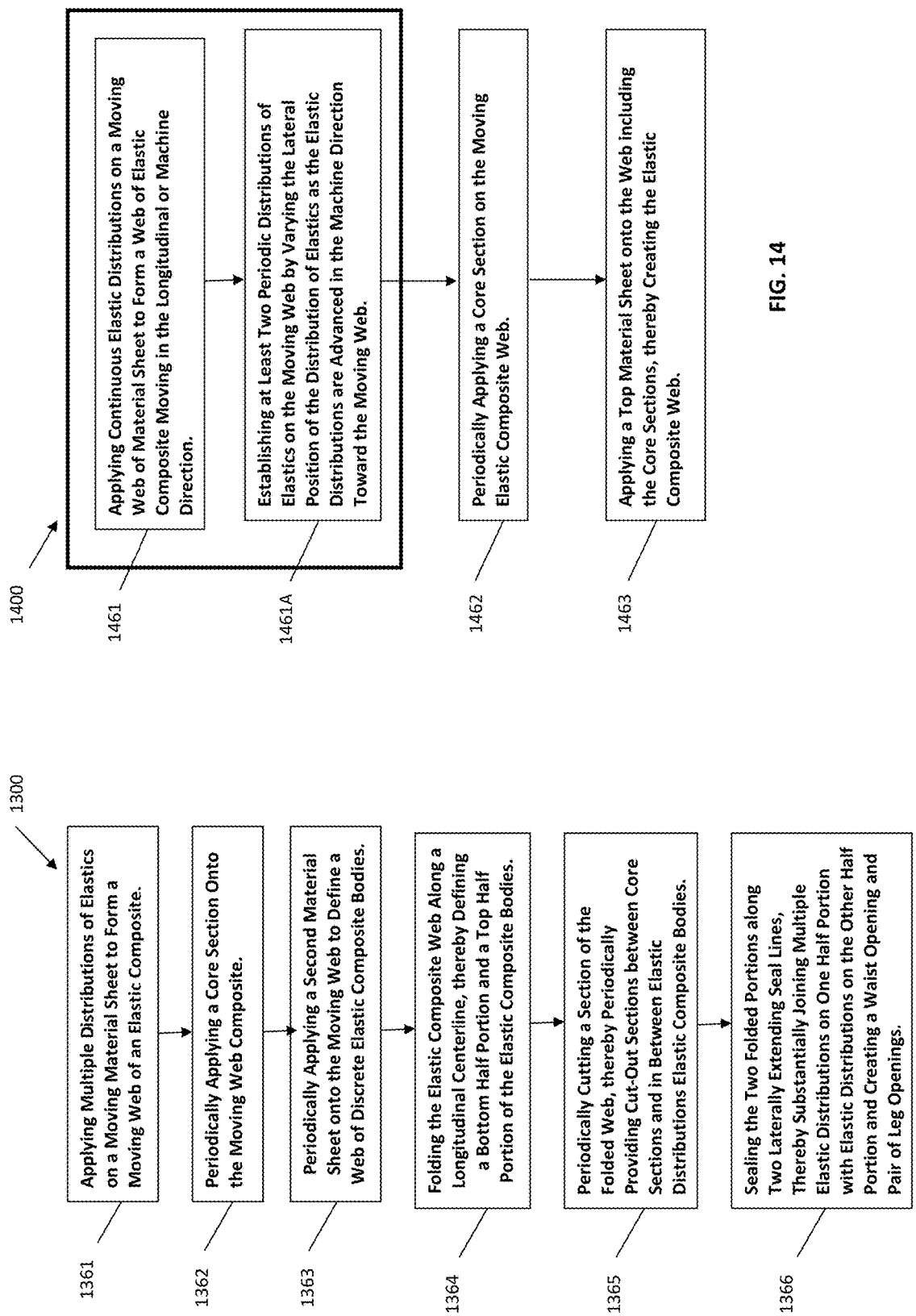

ARTICLE WITH ELASTIC DISTRIBUTION AND SYSTEM AND METHOD FOR MAKING SAME

The present application is a Continuation application of U.S. application Ser. No. 14/946,528 filed on Nov. 19, 2015 (now allowed), which is a Continuation application of U.S. application Ser. No. 13/200,100 filed on Sep. 16, 2011 (now U.S. Pat. No. 9,205,003), which claims the benefit of U.S. Provisional Application Ser. No. 61/403,488, filed on Sep. 16, 2010, which disclosure is hereby incorporated by reference for all purposes and made a part of the present disclosure.

BACKGROUND OF THE INVENTION

The present invention relates generally to an elastic composite and a disposable absorbent article incorporating an elastic composite. The invention also relates to elastic composite webs, systems, and methods suitable for making the same. Aspects of the invention are particularly suited for, or related to, disposable absorbent articles such as baby diapers, training pants for infants and young children and adult incontinence diapers and pants. Specific embodiments of the invention may provide a web of elastic composite, an elastic composite or body, or elastic distribution patterns within these products, which, in turn, may improve the product's fit and comfort, its support and sealing capabilities, enhance the cost and manufacturability of the product and\or enhance the aesthetic qualities of the product.

Disposable absorbent articles contemplated by the invention include training pants, pull-on diapers, disposable underwear, and adult incontinence garments. As for training pants, these garments are used by young children to facilitate a child's transition from using diapers to wearing regular underpants (i.e., during toilet training). Training pants and other disposable pull-on pants have closed sides such that the user or caregiver raises the garment about the user's legs to wear the garment and slips the garment downward about the user's legs to take it off. These articles and garments are collectively referred to herein as "absorbent pants" or "pants products."

Elastic members may be incorporated into different parts of an absorbent garment. For example, elastic members may be positioned longitudinally along a diaper, generally outboard of the absorbent core to effect a seal around the buttocks, legs, or both of the users. In addition, several elastic members (e.g., in the form of elongated elastic threads or strands) may be positioned laterally throughout the waist regions (including the side waist regions) of an absorbent garment. The resulting elastication allows the garment to stretch when it is put on and when it is worn. The elastication allows the garment to accommodate variations in waist size and leg size of the user, while fitting snugly about the waist and legs.

When elastic members are incorporated into a part or area of an absorbent garment, that part or area typically becomes a distinct, functional component of the garment. These elastic components include the side panels or ear portions, the waistband, and fastening tabs. Due in part to its multi-component construction, elastic composites may require a dedicated sub-process for manufacture which must be accommodated by the greater garment manufacturing process. Alternatively, the elastic composite may be manufactured independently or simply, manufactured in a separate sub-process detached from the central garment manufacturing system. In either case, a source of the elastic composite may be provided as input to the garment manufacturing process.

In most applications, the elastic composite has a significant impact on the fit and sealability of the garment, as well as the general appearance and construction quality of the garment. The design and construction of the elastic composite can also represent a significant portion of the cost of manufacturing the garment. It is, therefore, desirable to provide a functionally and/or aesthetically improved elastic composite or a cost effective system and method of making the elastic composite.

U.S. Pat. Nos. 7,462,172 and 7,361,246 provide background information on elastic composites (and the manufacture of such composites) of a type relevant to the present invention. Accordingly, these patent publications are also hereby incorporated by reference and made a part of the present disclosure, but only to the extent that incorporated subject matter provides background information and/or exemplary composites and processes suitable for use on, or with, the present inventive composites, systems, and methods. Thus, the incorporated subject matter shall not serve to limit the scope of the present invention. It should be noted that while these prior patent publications provide some discussion on making elastic composites and then incorporating same into absorbent articles, the present invention is, in one respect, more particularly directed to providing an improved system and method of making an elasticized absorbent article and/or a web of elastic composite bodies. More specifically, one directive of the present invention is to provide a method and system, whereby and wherein the elastic composite and its formation are seamlessly integrated into the method of making the article and into the elasticized article itself.

SUMMARY OF THE INVENTION

For purposes of the present description, the terms "elastic composite", "elastic composite body", and "elasticized article" refer to a multi-layer or multi-component construction that incorporates an elastomeric material(s) or elastic member(s). In this construction, a plurality of elastic members, such as threads or strands, are connected to or disposed adjacent one or more materials, e.g., backsheet and topsheet. In this way, the elastic members impart elasticity to the connected or adjacent layers and thus, to that part of the garment or article. Such an elastic structure may be a distinct attachable component of the garment or article, or may be a distinct portion or section of the garment body article or a larger, unitary component of the garment.

Further, as used herein, the term "web" refers to an extended, conveyable sheet or network. The term "substrate" refers to a supporting web, sheet, or layer, such as a web or layer of backsheet onto which elastics adhere or are otherwise supported. Further, a web may be of an elastic composite and/or provide a plurality or series of discrete elastic composite bodies. In embodiments described herein, such elastic composite bodies may be separated from the web to form the basis of a disposable absorbent article such as a diaper or absorbent pants.

In one aspect of the present invention, an elasticized disposable absorbent article is provided in the form of absorbent pants. The absorbent pants include an elastic composite body, a backsheet, a topsheet, an absorbent core between the backsheet and topsheet, and multiple elastic distributions between the topsheet and backsheet. Furthermore, the elastic composite body has a front end edge, a rear end edge, and two lateral side edges each having a top segment, a bottom segment, and a non-linear cut-out section therebetween. The absorbent article also includes a waist opening defined by the end edges, a pair of leg openings each defined, at least partly, by the cut-out section of one of the lateral side edges, and a pair of side seams each defined by a joining of the top and bottom segments of one of the lateral side edges. The elastic distributions are substantially joined at the side seams to form a substantially annular elastic region about each leg opening.

In further embodiments, the elastic composite body also includes a pair of elastic distributions joined at the side seams to form a substantially annular elastic region about the waist opening. Preferably, the elastic composite body further includes a pair of elastic distributions each extending across the composite body and substantially joining the other at the side seams to form the substantially annular elastic region about the leg opening.

In another aspect of the invention, a method of making elasticized absorbent pants preferably commences with applying multiple distributions of elastics on a moving material sheet to form a moving web of an elastic composite. Each one of a core section and a second material sheet is periodically applied onto the moving web to define a finished web of discrete elastic composite bodies. The steps leading to delivery of a finished web of discrete elastic composite bodies may be referred to as the step of joining the elements or layers of the target elastic composite web. In a subsequent step, discrete absorbent pants or articles are shaped from the finished web. The shaping step may include joining each of a bottom half portion and a top half portion of each composite body to form a plurality of substantially continuous elastic distributions in the elastic composite body. In a further embodiment, the joining step forms annular elastic regions about a waist opening and/or each of a pair of leg openings. In further embodiments, the joining step is preceded by the step of folding the finished web along a longitudinal centerline and the joining step includes sealing the two half portions along two side seams to define at least a waist opening. In another embodiment, the joining step is preceded by the step of periodically cutting a cut-out section of the finished web at a location adjoining adjacent elastic composite bodies such that, after the joining step, each lateral boundary of the elastic composite body consists of a lateral side seam and the cut-out section. The shaping step further includes severing the finished web along a cut line bisecting the cut-out sections. In a more preferred embodiment, the joining step precedes the severing step so that the severing step immediately produces elastic absorbent pants having a waist opening, a pair of leg openings, and multiple continuous elastic distributions extending through two lateral seal lines or side seams.

According to another aspect of the invention, a method of making an elastic composite web, from which elastic composite bodies of absorbent pants may be separated, commences with the steps of conveying a continuous web of material sheet and applying multiple continuous distributions of elastics on the moving web to form a web of elastic composite, the elastic distributions generally extending in the machine direction. The method also entails periodically applying a core section on the moving elastic composite web and, then, continuously applying a top material sheet on the web including the core sections. In the step of applying continuous distributions of elastics, at least two periodic distributions of elastics are established on the moving web by varying the lateral position of the distribution of elastics as the distributions are advanced in the machine direction toward the moving web of elastic composite. In further embodiments, the step of applying the continuous distributions includes periodically varying the lateral position of the elastic distribution prior to engagement with the material sheet and further yet, periodically varying the lateral position to establish two elastic distribution patterns on the moving web of elastic composite that periodically trace an annular elastic region. In further embodiments, the method includes a step of periodically severing one or more of the elastic distributions so as to prelocate gaps in the elastic distribution on the moving web of elastic composite. In further embodiments, each of the elements or layers of a web of elastic composite bodies is delivered in-line or in the machine direction, and further, at or about a joining station or mill of the system.

In another aspect of the present invention, a system and process are provided for delivering a web of elastic composite bodies. The system and process provides a central forming region or joining mill that receives all of the elements or layers of the target elastic composite and joins these elements in accordance with a specific sequence. Preferably, all of such elements are inputted into the mill and received in the machine direction. The output of the joining step is a web of elastic composite bodies that may be further manipulated to achieve a series of disposable absorbent articles. Post-joining steps may include folding, sealing, and/or severing of the elastic composite bodies.

BRIEF DESCRIPTION OF THE DRAWINGS

So that the manner in which the features and advantages of the present invention may be understood in more detail, a more particular description of the invention briefly summarized above may be had by reference to the embodiments thereof which are illustrated in the appended drawings that form a part of this specification. It is to be noted, however, that the drawings illustrate only various exemplary embodiments of the invention and are therefore not to be considered limiting of the invention's scope as it may include other effective embodiments as well.

FIG. 1A is a simplified illustration in isometric view of a disposable absorbent article according to the present invention;

FIG. 1B is a cross-sectional view an elastic composite or elastic composite web according to the present invention;

FIG. 2A is a simplified diagram in side view of a system or apparatus for making an elastic composite or elastic composite web according to the present invention;

FIG. 2B is a plan view of the system in FIG. 2A;

FIG. 13 is a flowchart diagram for a method of making an elasticized absorbent article, according to one embodiment of the present invention;

FIG. 14 is a flowchart diagram for a method of making an elastic composite web, according to an embodiment of the present invention;

DETAILED DESCRIPTION OF THE INVENTION

Figure 2C:
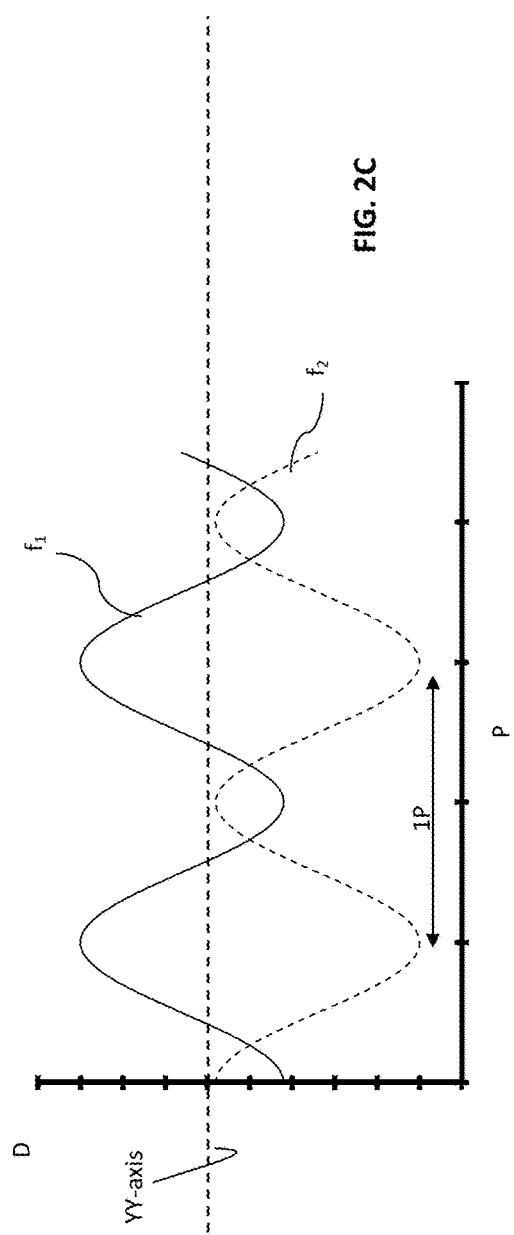
FIG. 2C is a graphical diagram of an exemplary periodic function reflecting directive lateral motion by elastic guides in FIGS. 2A-2B to produce a dual elastic distribution pattern on an elastic composite web, according to the present invention.

The present invention will now be described more fully with reference to the accompanying drawings, which illustrate various exemplary embodiments. The invention may, however, be embodied in many different forms and should not be construed as being limited by the illustrated embodiments set forth herein. Rather, these embodiments are provided so that this disclosure will be thorough as well as complete and will fully convey the scope of the invention to those skilled in the art and the best and preferred modes of practicing the invention. For example, many of the exemplary descriptions provided herein are concerned with training pants for infants and young children. Aspects of the invention described may, however, be equally applicable to designs for and the manufacture of, baby diapers, adult incontinence products and other similar products.

FIG. 1A illustrates a first embodiment of the present invention, in the form of a disposable absorbent training pants 101. The upright absorbent pants 101 is formed from an elasticized composite body 136 with a first or front half portion rotated about a symmetrical line to join a substantially identical second or rear half portion. The two half portions are joined at a pair of sealed side seams 130. Each side seam 130 consists of a first or bottom segment of a side edge 106 joined to a second or top segment of the same side edge 106 (as will be further explained below). The resultant absorbent pants 101 has a front longitudinal waist edge 102, a rear longitudinal waist edge 103, and the pair of sealed side seams or seals 130 each on a lateral side of the absorbent pants 101. To facilitate the present description of the invention, the pants body 136 is sometimes described as having an upper waist region 124 and a lower waist, leg, and crotch region (lower region 126). The absorbent pants configuration 101 is also provided with a fluid distribution and storage construction or absorbent core 105 on the inside of the pants 101 and about a crotch region 134. In one aspect of the invention, the forming of the two lateral side seals 130 immediately creates the absorbent pants configuration 101. This absorbent pants configuration 101 includes a waist opening 132 defined by the joining of the two waist edges 103 to complete a continuously encircling waist edge. The pant configuration 101 further includes two leg openings 104 formed by the joining of the half portions (as will also be further explained below).

The pants configuration 101 also includes the lateral side seams 130. The side seams 130 may be provided by a permanently bonded seal or a refastenable seal. A permanent side seal may be achieved, for example, through the use of adhesive bonding, thermal bonding, ultrasonic bonding or any other suitable bonding mechanism. A refastenable side seal may be achieved through the use of adhesives, hook and loop materials or other refastenable mechanisms.

To enhance the comfort and fit of the absorbent article, as well as its capacity to contain fluid and minimize the occurrence of leakage of fluid through the waist and leg openings 132, 104, the disposable absorbent article 101 is provided with strategically-placed elastomeric materials 120. In a preferred embodiment, these elastomeric materials consist of strands or yarns of elastic thread such as natural rubber, latex strands or synthetic elastomers such as Lycra or Spandex yarns. Other suitable elastomeric materials include, but are not limited to, stretchable elastomeric films, elastomeric ribbons, elastomeric nonwovens and elastomeric adhesives. For purposes of this description, any discussion of the elastomeric materials will be confined to the use of elastomeric strands or yarns, which may referred to as elastic strands or elastics. It will become apparent, however, that these elastomeric materials may be readily substituted with many other types of elastomeric material.

The absorbent pants 101 in FIG. 1 incorporate multiple distributions of elastic strands 120 in the upper waist region 124 and in the lower waist, leg and crotch regions (lower region 126). These distributions of elastic strands render the composite body 136 with strategically localized and advantageously configured elasticity. Upon sealing of the side edges 106, this feature translates directly and readily to the resultant absorbent pants 101 and ultimately, to the pants 101 as worn by the user. Accordingly, the pants 101 of the invention may be referred to as an elasticized disposable absorbent article 101. To elaborate, each of the elastic distributions in the absorbent pants 101 define a substantially annular area or region of elastics or elasticity. In the upper waist region 124, a set or distribution 110 of the elastic strands 120 is arranged generally circumferentially about the waist opening 132 and just below the joined waist edges 102, 103, and thus, encircles the waist of the user. Preferably, the elastic strands 120 are mutually spaced apart and generally parallel with the waist edges 102, 103. Accordingly, the absorbent pants 101 is equipped with a particularly advantageous annular region of elastic and elasticity snugly encircling the entire waist of the user and, acting therewith, to effectively seal the waist opening 132. In the lower region 126, multiple distributions of elastic strands 120 extend substantially completely about the leg openings 104 and the crotch region 134. One set or distribution 111 of elastic strands 120 encircle the leg opening 104 and forms an elasticized annular area or region thereabout. A third annular area or region of elastics is generally positioned centrally in the crotch region 134.

The elastic annular regions about the waist opening and the leg openings are advantageously maintained substantially all the way around the sealing subject (i.e., the potential opening between the waist and the waist edge 102,103 and the potential openings between the thigh and the circular side edge of the article 101). Moreover, the strength and direction of the elastic forces are maintained generally uniform about the openings. A more effective and more reliable seal is achieved because all potential leakage points around the opening are addressed. Uniformity in the elasticity about the waist or thigh also helps to prevent uneven fit, which can lead to a poor seal. Notably, the elastic distributions 110, 111 in the composite body 136 extend substantially all the way from one side edge to the opposite side edge (as explained below) and, upon formation of the pants configuration 101, extend substantially continuously (without ends) about the article 101. It should be understood, however, that the elastics of the annular regions do not necessarily have to touch or overlap. It is sufficient for the ends of elastics to be proximate to opposing ends so as to effect generally uniform elasticity about the sealing subject or edge, substantially similar to an actual ring of elastic placed thereabout.

It should be noted that the elastic strands 120 about the leg opening 104 may overlap into the crotch region 134. It should also be noted that the elastic strands 120 in the upper and lower regions 124, 126 are not necessarily mutually exclusive and elastic strands in one region may overlap and intersect elastic strands in the other region.

In one aspect of the present invention, the disposable absorbent article 101 having one or more annular regions of elastics or elasticity may be made utilizing a single, unitary elastic composite body 136 (or prior to making the pants configuration 101, simply elastic composite 136). FIG. 1B is a cross-sectional view of an exemplary elastic composite 136 specifically for the absorbent pants 101 of FIG. 1B. Among other things, this view describes the multiple distributions of the elastic strands 120 in the elastic composite 136 utilized in the absorbent pants 101 according to the present invention. The elastic composite 136 has a first or bottom edge 102 and a second or top edge 103 (which ultimately define the waist edges 102, 103 in the pants configuration 101). The composite 136 also has an outer, fluid impermeable backsheet layer 107, an optional intermediate layer 108, a fluid distribution and storage construction or core 105 and a fluid permeable topsheet 109. The fluid impermeable backsheet layer 107 may be selected from a range of materials that include hydrophobic, fluid impermeable nonwoven materials, breathable and non-breathable polyethylene films or laminates of these materials. The optional intermediate sheet layer 108 may also include hydrophobic, fluid impermeable nonwoven materials, breathable and non-breathable polyethylene films, and laminates of said materials or other suitable materials. As shown in FIG. 1B, the two sheet layers 107, 108 help retain the elastic distributions 110, 111 in place, although, in some embodiments, the elastic distributions are adhered only to the surface of the backsheet layer 107. The fluid distribution and storage construction or absorbent core 105 may be composed of nonwoven materials, aperture films, tissue, cellulose fluff pulp, superabsorbent polymer particles or fibres or any other materials that can be utilized to distribute and absorb the fluid and solid insults passed into the article when it is used. Furthermore, fluid permeable topsheet 109 may comprise a hydrophilic, fluid permeable nonwoven web or an apertured material.

For the absorbent pants 101 of FIG. 1, the exemplary elastic composite 136 reveals a first distribution 110 of elastic strands 120 directed along each of the first edge 102 and the second edge 103. In this embodiment, a grouping of six spaced apart strands 120 is generally bunched together along the edges 102, 103, while three individual strands 120 are located inwardly of these strands 120. The spacing between the three individual strands 120 is wider than that of the first six strands 120. This spacing of strands 102, 103 corresponds with the spacing of the strands 120 in the upper region 124 of the disposable absorbent article 101 of FIG. 1A which concentrates elasticity near the edges 102, 103. The elastic composite 136 also features the two other distributions 111 of elastic strands 120. Two distributions 111 of five strands 120 each are located inwardly from the two outside distributions 110, as shown in FIG. 1B. As will be further described below, these two distributions 111 correspond with the elastic distributions 111 about leg openings 104 and in the crotch region 134 of the disposable absorbent article 101.

Figure 3:
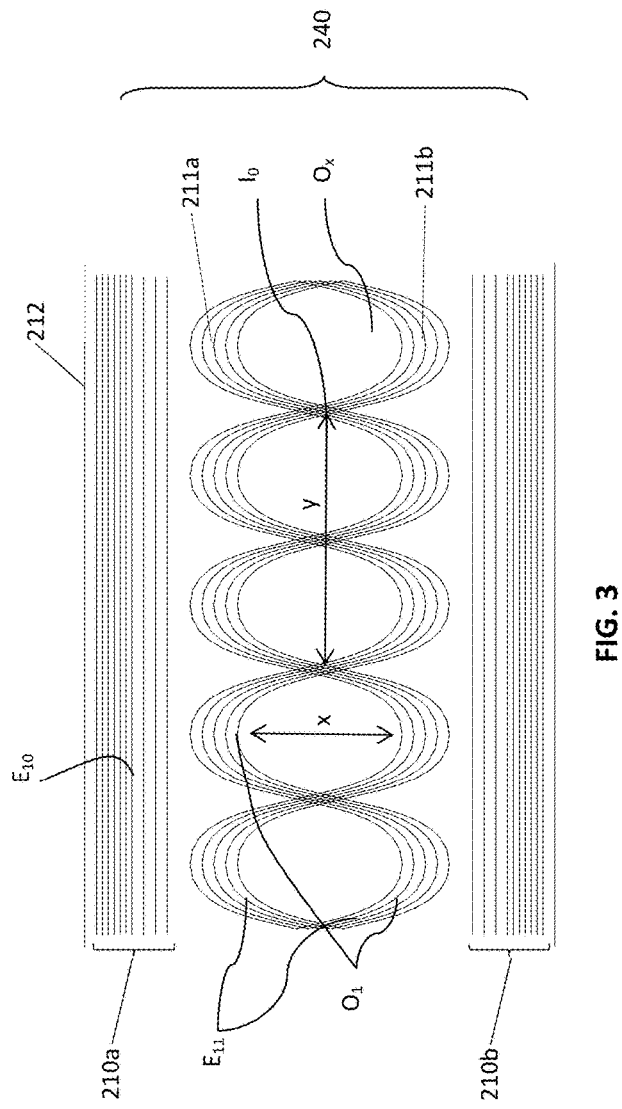
FIG. 3 is a simplified illustration of an elastic composite web according to the present invention.
Figure 4:
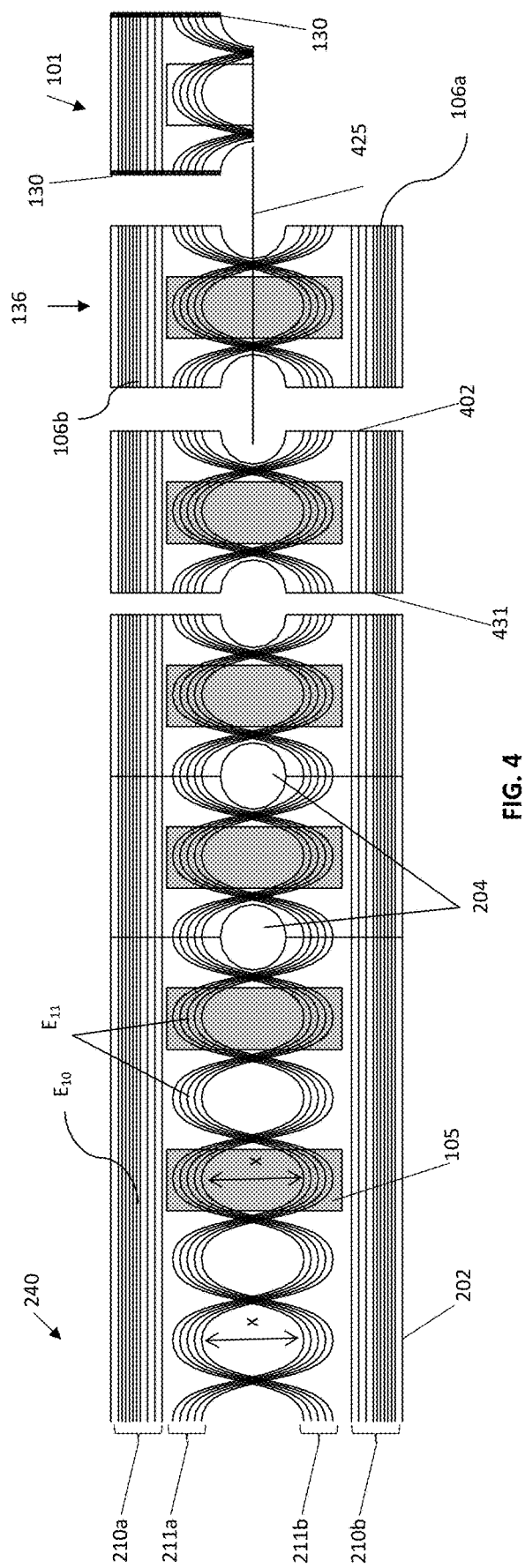
FIG. 4 is a simplified illustration of a web-based process for making the disposable absorbent article in FIG. 1, according to the present invention.

The simplified illustrations of FIGS. 2A and 2B describe a system 150 and method for making a web 240 of the elastic composite 136. More specifically, the system 150 and method are utilized for incorporating the desired elastic distributions 110, 111 described above in an elastic composite 136 and in a composite web 240 (and ultimately, in an absorbent article 101), according to the invention. The illustrated method provides an initial sub-process in making the elastic composite 136 and the disposable absorbent article 101 in FIG. 1. FIG. 4 illustrates the subsequent and remaining stages in this method. Both FIGS. 3 and 4 depict a unitary elastic composite web 240 that is particularly suited for making disposable absorbent articles 101. As will be described, the composite web 240 can contain and present four continuous, machine-directioned distributions of elastic strands that trace a specific, advantageous pattern. At least two of the distributions are described by a periodic function featuring a trough and a summit. The other two distributions are preferably maintained along a direct path.

Referring now to FIGS. 2A and 2B, the inventive system 250 and method convey, append, and manipulate an elastic composite web 240 in a substantially linear process and in the machine direction. For purposes of description, the web 240 is referred to as having a first or bottom edge 202, a second or top edge 203 spaced apart from the first edge 202 in the cross-machine direction and generally parallel therewith, a cross-machine width defined between the two edges 202, 203, and a longitudinal centerline YY. In some descriptions, the cross-machine direction across the web 240 and components supporting the inventive web 240 may be referred to as a lateral direction, while the machine direction may be described as corresponding to a longitudinal direction. Preferably, the elastic composite web 240 is advanced at a uniform rate of speed in the longitudinal or machine direction.

In a preferred embodiment, the method initially requires the separate, continuous conveyance of each of six elements of the elastic composite 136 to a joining mechanism such as a nip roller 218 (see e.g., FIG. 2A). These elements include a first material sheet 212, a second material sheet 213, a first set 210a of pre-tensioned elastic strands along the top edge 203, and a second set 210b of pre-tensioned elastic strands along the bottom edge 202. The first and second sets 210a, 210b of elastics strands are aligned in mutually parallel alignment but spaced apart specifically according to a predetermined arrangement. In this specific embodiment, the first and second sets 210a, 201b are mirror images of one another. Additionally, two other sets 211a, 211b of pre-tensioned elastic strands are conveyed along a machine direction laterally inwardly of the first and second sets 210a, 210b of pre-tensioned elastic strands. As best shown by FIG. 2A, both the first and second sets 210, 211 of elastics are preferably introduced and conveyed toward the nip roller 218 along the horizontal plane of the web 140. The two inwardly sets 211a, 211b of elastics are also introduced on the same web plane. The two material webs 212, 213, are on the other hand, preferably initiated from generally above and below the web plane, respectively (hence, sometimes referred to as upper and lower material webs or sheets).

The elastic strands may be received in a tensioned state by means of any suitable feeding and tensioning device positioned upstream of this process (not shown). The initial lateral positions of the elastic strands, as well as the spacing between adjacent elastic strands, are initially fixed by elastic guides 215. These fixed elastic guides 215 are mounted on two rods 219, as shown in FIGS. 2A and 2B. The elastic guides 215 typically comprise rollers, eyelets or any other suitable means for conveying and guiding the pre-tensioned elastic strands. A second set of elastic guides 216a, 216b are mounted on movable rods 221 downstream of the fixed rods 219. Each of these two movable elastic guides 216a, 216b engages one of the two inward sets 211a, 211b of elastic strands. Preferably, the movable rods 221 and movable guides 216a, 216b are positioned above and below the web plane, respectively. Thus, while a first set 211a of elastics is introduced along the web plane, it is directed slightly above the web plane a short distance after introduction. Similarly, the other set 211b is directed slightly below the web plane after introduction. This adjustment occurs before the two sets 211a, 211b of elastics are engaged by conveying means 217 and advanced to the nip roller 218.

It should be noted that the specific components of the system 250 shown in the Figures may be substituted with other suitable means or components. For example, in alternative systems, stationary guides or eyelets may be mounted on a fixed frame. Further, the movable guides may be mounted or associated with mechanical arms, cam systems, and other suitable mechanisms.

The sets 210a, 210b of elastic strands are distributed in a generally parallel alignment toward the nip roller 218. These elastic strands are analogous with the distribution 110 of elastic strands present in the upper waist region 124 of the absorbent article 101 in FIG. 1 and are distributed in parallel relationship with the top and bottom edges 202, 203 composite web 240. For the absorbent pants 101 of FIG. 1, the arrangement of the sets 210a, 210b of elastic strands must be identical. Other article designs may be provided, however, wherein the arrangements are not identical and one set may include more elastic strands than the other set. Also, the spacing and concentration of the elastics may, in other designs, differ to achieve a specific function or aesthetic attribute. Although such designs may deviate from the preferred arrangements for annular elastic regions, as described above, it is expected that such alternate designs will not deviate completely and that some aspects of the preferred designs will be retained (in accordance with the invention).

The moveable elastic guides 216a 216b are configured to move in a direction orthogonal to the machine direction of the web 240 and serve to change and direct the placement of the sets 211a, 211b of elastic strands into the nip roller 218 and adjust the lateral spacing of the elastic strands. Accordingly, the two inward sets 211a, 211b of elastics may be referred to as variable (as opposed to "fixed") sets of elastics. By vertically spacing the two variable sets 211a, 211b of elastics (as described above), the two sets 211a, 211b can move laterally without interference from the other. In this embodiment, for example, the two sets 211a, 211b of elastics laterally cross so that a bottom set of elastics arrives at the nip roller 218 as the top side set while the other set becomes the bottom side set.

In a preferred embodiment, the elastic guides 216a and 216b are mounted on a reciprocating mechanism such that the elastic guides are continually reciprocating in a lateral direction (orthogonal or transverse to the machine direction of the process). The guides 216a, 216b may be carried on the same continuous belt or track and move together at all times. In other embodiments, the guides 216a, 216b may be driven independently of one another, particularly if the pattern of on elastic distribution is greatly independent of the other. Suitable driving mechanisms can include a cam based mechanism, a servo driven mechanism or a hydraulic mechanism. Preferably, the motion of the elastic guides 216a and 216b is described by a periodic function, in which a relative displacement of the elastic (or elastic guide) is a function of time (or a length of the web) plus a discrete increment (P, period). This displacement function expresses the periodic shape or pattern of the distributed elastics.

The graphical illustration of FIG. 2C describes an exemplary periodic function reflecting the lateral displacement (D) of the movable guides 216a, 216b over a period of time (P) (which is proportional to the width of the elastic composite 136 relative to machine speed). The two separate functions f1, f2 show the relative lateral movement of the guides required to produce the dual elastic distribution patterns on the web. As shown by the graph, the two elastic guides necessarily cross twice during each period. The multiple crossings translate to the generation of a series of elastic annular regions on the composite web, or at least two annular regions per period (P) or elastic composite body 136.

The upper and lower sheets 212, 213 are also directed by conveyance means 217 toward the web plane and then to nip roller 218. Thus, the two two sheets 212, 213 and the four sets 210, 211 of elastics arrive substantially together at the nip roller 218. The upper and lower sheets 212, 213 served to sandwich, entrap and hold the elastic strands in position after passing through the nip roller 218. The resultant web 240 of elastic material and material webs is secured using any suitable bonding means which include, adhesive, ultrasonic or thermal bonding (not shown). In the case of adhesive bonding, the adhesive could be applied to the upper and lower sheets 212, 213 or applied directly to the sets 210, 211 of elastic strands at any point prior to the elastic strands and upper and lower sheets meeting and combining at the nip roller 218.

FIG. 3 illustrates the continuation of the system 250 and method of making the disposable absorbent article 101 illustrated by FIGS. 2A, 2B. The system 250 and method of FIGS. 2A and 2B output an elastic composite web 240 that includes an upper sheet 212, a lower sheet not shown, but directly underlying the upper sheet 212, and distributions E10, E11 of elastic strands across the cross-machine direction width of the web 240. The two variable distributions E11 of elastic strands disposed in the middle are directed by means of the periodic, lateral motion of the elastic guides 216a, 216b in FIG. 2 (and its periodic function), which in this example, result in a sinusoidal pattern. The pattern may also be described as a series of annular elastic regions O1 or areas formed by the troughs and valleys of the two variable distributions E11 of elastics. Other linear and non-sinusoidal patterns may be produced by this process; but, for the purposes of this exemplary description, the sinusoidal pattern is employed. One set 211a of elastics is distributed in a first sinusoidal pattern E11 and are overlapped with the elastics of the second set 211b which are distributed in a second sinusoidal pattern E11. In this example, the first and second sinusoidal patterns are mirror images of each other. The two distributions E11 also define a region Ix at which one set overlaps and intersects the other. The degree to which the elastic strand patterns overlap can be measured and is, hereafter, described as the variable "X". The wavelength of the sinusoidal pattern can also be measured and is hereafter recorded as the variable "Y". Both variables "X" and "Y" are process parameters that may be adjusted by changing various process parameters such as machine speed, reciprocation speed and reciprocation depth.

FIG. 4 illustrates a process or conversion step for further modifying and then converting the elastic composite web 240 of FIGS. 2 and 3 into the disposable absorbent article 101 in FIG. 1A. As shown in FIG. 4, the sub-process proceeds downstream from left to right whereby the initial step may be described as receiving an output (the elastic composite web 240) from the system 250 and sub-process of FIGS. 2A and 2B. A fluid distribution and storage construction or core 105 is applied centrally over one of the overlap regions Ox of the two sets 211a, 211b of sinusoidal elastic strands. The elongated core 205 is applied and positioned laterally with the length of the core 205 being deposited on the web 240 in the cross-machine direction. In this embodiment, the core 205 is situated between the upper and lower distributions E11 of elastics. Simultaneous with or immediately after the application of the core 205, a material sheet 209 (not shown) is applied over the core 205 and the web 240. This material sheet becomes the topsheet in the disposable absorbent article 101. Additional features such as free-standing elasticised leg cuffs, fastening tapes and disposal tapes may be added to the construction at this stage.

In a subsequent step or stage in the process, preferably circular holes 204 are punched or cut in the web 240. In this embodiment, the holes 204 are punched centrally inside of the elastic annular regions O1, but on the overlap region Ox. As shown in FIG. 4, the holes 204 are also in longitudinal alignment with the intersections Ix of the elastic strands and with the wavelength distance "Y" of the sinusoidal patterns. The cutting of the holes 204 leads to the provision of the leg openings 104 in the disposable absorbent article 101. It is, therefore, an important requirement of the disposable absorbent article 101 that the wavelength "Y" of the sinusoidal pattern is equal to the width of the finished article 101.

The next step in the production process entails cutting or severing the continuous composite web 240 across the cross-machine direction width and along cutting lines 431. This end cut can be accomplished by a number of mechanisms known to those skilled in the art, including a die cutting process or a water-jet cutting process. The position of the end cut is determined relative to the wavelength "Y" of the sinusoidal pattern. Notably, cutting lines 431 bisect each hole 204 and alternating elastic annular regions O1. The cutting lines 431 are also spaced on either side of the core 205.

Upon separation, discrete, individual elastic composites 136 are formed. The elastic composite 136 now has a longitudinal (lengthwise) centerline that bisects the elongated core 105. Further, the composite 136 has two lateral side edges 106a, 106b along the original cutting lines. The side edges 106a, 106b consists of a top segment and a bottom linear segment. The non-linear cut-out section is positioned intermediate the two segments and is intended to form the leg openings. The elastic composite 136 also feature half elastic annular regions extending to each side edge 106a, 106b, which were severed by the cutting lines, and complete annular elastic annular regions in the center. The elastic composite 136 also has a core 105 situated centrally over the central elastic annular region.

Finally, the elastic composite 136 is folded along fold line 425 which corresponds to the longitudinal axis YY of the web 140. The elastic composite 136 in this embodiment is symmetric about this axis YY. Accordingly, when folded, each feature or portion on the bottom half match and cover the exact same feature or portion on the top half. The result is the disposable absorbent article 101 in FIG. 4 (and FIG. 1A). In the flat and folded state, the article 101 now displays a quarter of each leg 104 hole and a quarter of each half-annular region on the side edges 106a, 106b. To finalize the absorbent pants construction, the matching side edges 106a, 106b are sealed (seals 130), while the matching upper-lower edges 102, 103 and the quarter-leg holes are not. The specific manufacturing process for this embodiment employed a high "X" value.

Figure 5:
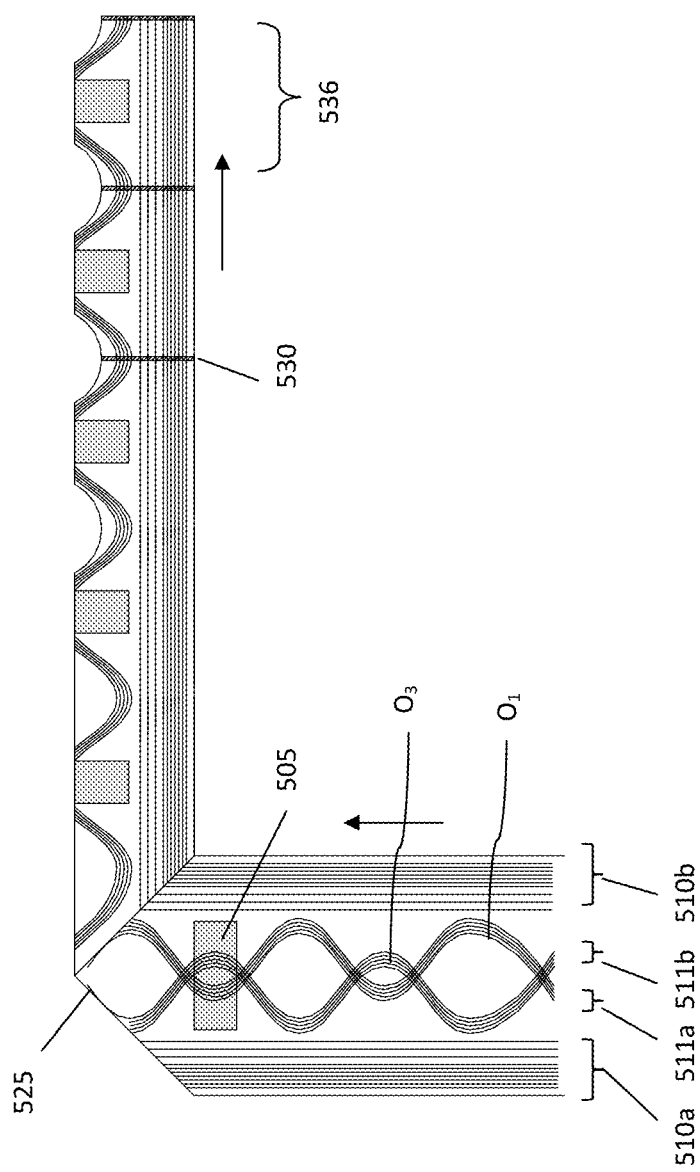
FIG. 5 is a simplified illustration of a web-based process for making a disposable absorbent article, according to an alternative embodiment of the present invention.

The process described with reference to FIGS. 2-4 is one example of the process of making the inventive absorbent article. It is not required that the steps described are completed in the order described. It is possible, and may in some circumstances be preferred, that the steps are completed in a different order or that some of the steps may be completed simultaneously FIG. 5 is a simplified representation and schematic illustrating a web 540 of elastic composite, as well as a method or process of making the elastic composite web 540 and an absorbent article, all according to an alternate embodiment of the invention. The illustration provides the latter or downstream stages of the process, after introduction and application of sets 510a, 511A, 511b, 510b of elastics. Downstream of the nip roller (not shown), the elastic composite web 540 generally consists of two or three layers of sheet material and the desired elastic patterns and elastic annular distributions for the waist region and the crotch region. In this embodiment, the two variable distributions 511a, 511b of elastics trace a pattern and period that consists of a large (wide) elastic annular region O1 and an overlap region Ox' bounded therein and a small (close) elastic annular region O3 and its overlap region Ox."

In a downstream stage, a desired absorbent core section 505 is applied onto the elastic composite web 540, over the close elastic annular region O3. Then, a material sheet layer (of topsheet) is applied over the elastic composite web and the core 505, to provide an enhanced elastic composite web 540 having all of the major components desired of the inventive absorbent article. At this step, the elastic composite web 540 may be described as a web of elastic composite bodies. In one aspect of this embodiment of the invention, the resultant elastic composite web 540 is folded about the longitudinal centerline YY. As shown in FIG. 5, this folding step may be accomplished by diverting the conveyor run about 90 degrees and such that one half of the elastic composite web 540 also rotates 180 degrees onto itself. The result is a 90 degree turn at which one half of the longitudinally extending web 540 folds over and matches its mirror image. The folded web 540 reveals a series of one-half sections of the wide annular regions O3. Using a conventional puncher or cutter, leg holes 504 (or more particularly, half of the leg holes) may be punched out of the elastic composite web 540 at a location within the wide overlap region Ox' and in between core sections 504. In this embodiment, this semi-circle cut is made at the upper edge of the folded elastic composite web.

Furthermore, a sealing bond or line 530 is applied from the leg hole 504 towards the side edge, thereby describing the boundaries of a unitary elastic composite body 536 according to the invention. Preferably, sealing is achieved by ultrasonic bonding, thermal bonding, and the like. Finally, discrete units 536 of the elastic composite web 540 may be severed by cutting through the wide sealing or bonding line 530. In further embodiments, the sealing and cutting steps may be performed simultaneously. The result is an elastic composite web in the form of training pants, according to the invention.

Figure 6:
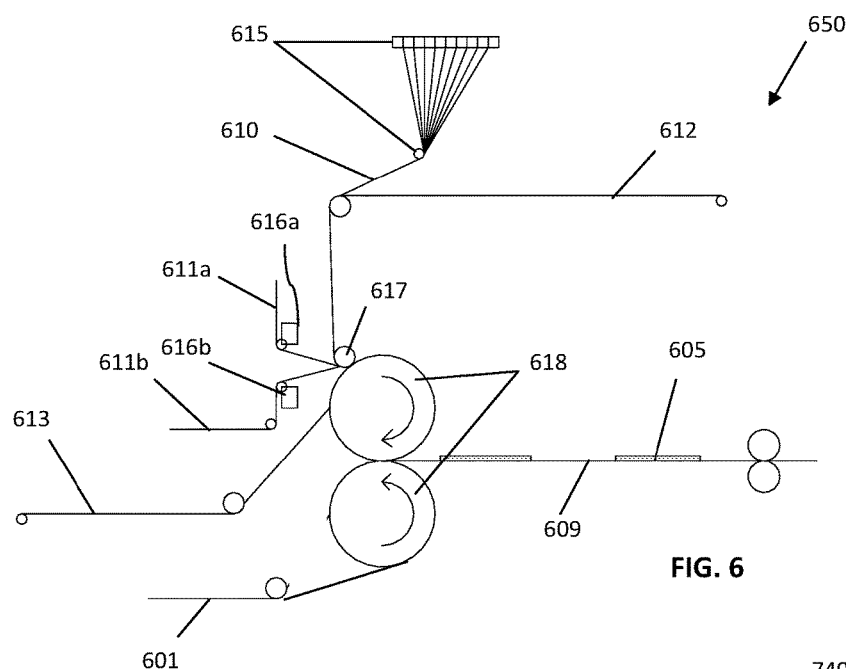
FIG. 6 is a simplified schematic of system for making the disposable absorbent article in FIG. 1, according to the present invention.

Now turning to the alternative illustration and schematic of FIG. 6, an alternative system 650 and method of making the disposable absorbent article utilizes a few different steps and sequences. A first material sheet 612 is conveyed separately by conventional means. Pre-tensioned elastics 610 (for the upper waist regions) are applied on the sheet 612, preferably near the side edges, as previously described. The resulting elastic composite 640 is then conveyed toward and by conveying means 617. Two sets 611a, 611b of elastics are also moved and conveyed toward the conveying means 617, utilizing elastic guides 616a, 616b. As before, the elastic guides 616a, 616b vary the lateral position of the set 211a, 211b of elastics in accordance with a periodic function and to elicit a preferred pattern. Thus, the elastic composite web 640 meets the two sets 611a, 611b of variable elastics at nip roller 618, thereby enhancing the original web 640 with preferred distributions of elastics. These preferred distributions include a series of annular regions, as in earlier-described embodiments.

Furthermore, a separate combination web 609 is applied on the elastic composite web 640 by a second nip roller 618. This subsequent application includes incorporation of a web of sheet material upon which core materials are already intermittently deposited, as shown in FIG. 6. The resulting output of the second nip roller 618 is an elastic composite web 640 having two material sheets and two sets of variable elastics and two sets of mutually parallel pre-tensioned elastics, similar to the outputs of the systems and processes of FIGS. 2A, 2B.

Figure 7:
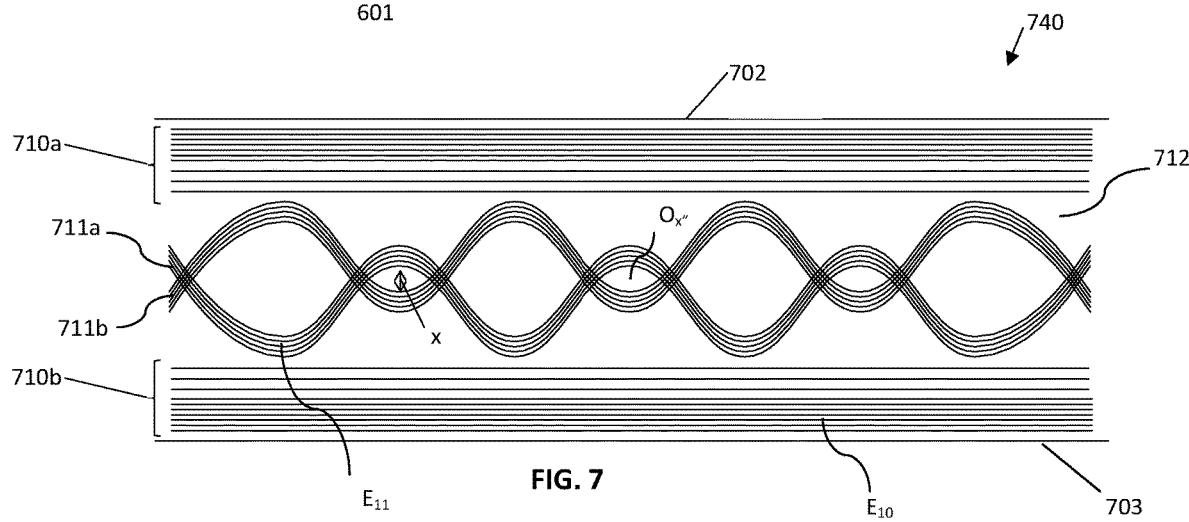
FIG. 7 is a simplified illustration of an elastic composite web employed in a web-based process for making a disposable absorbent article, according to the present invention.
Figure 7A:
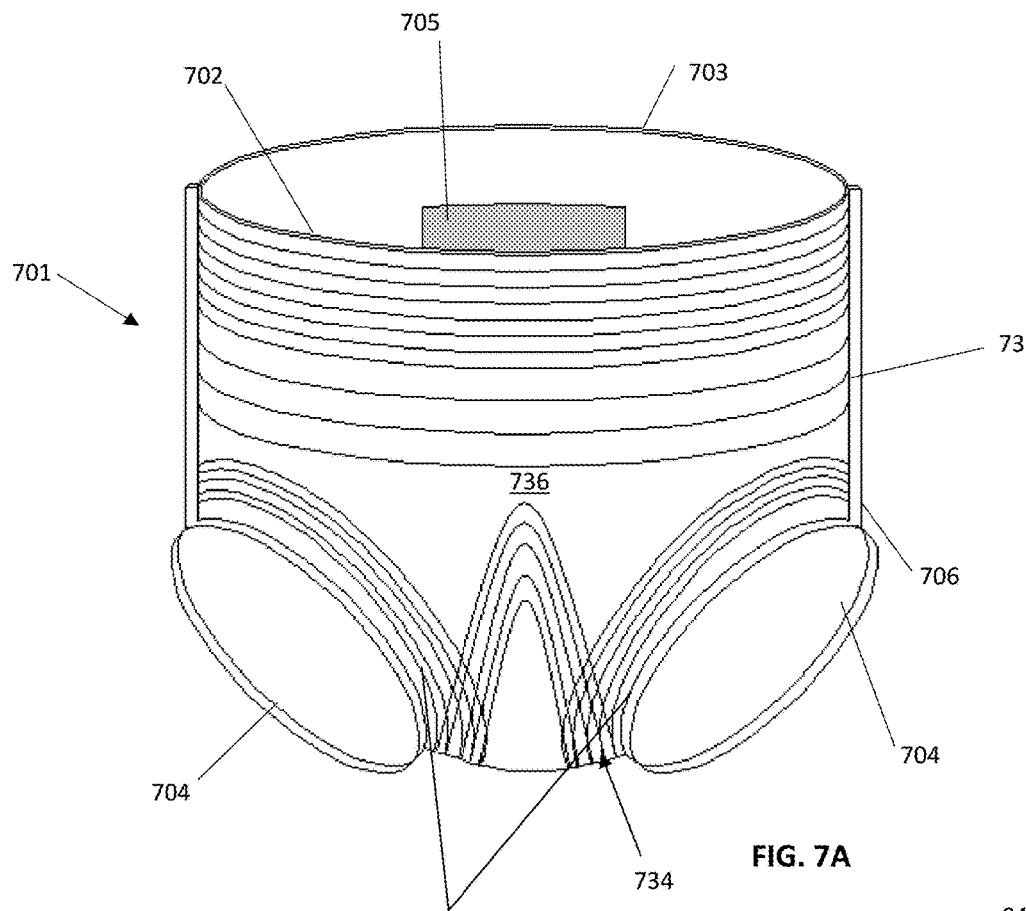
FIG. 7A is a simplified illustration in isometric view of a disposable absorbent article according to an alternative embodiment of the present invention.
Figure 8:
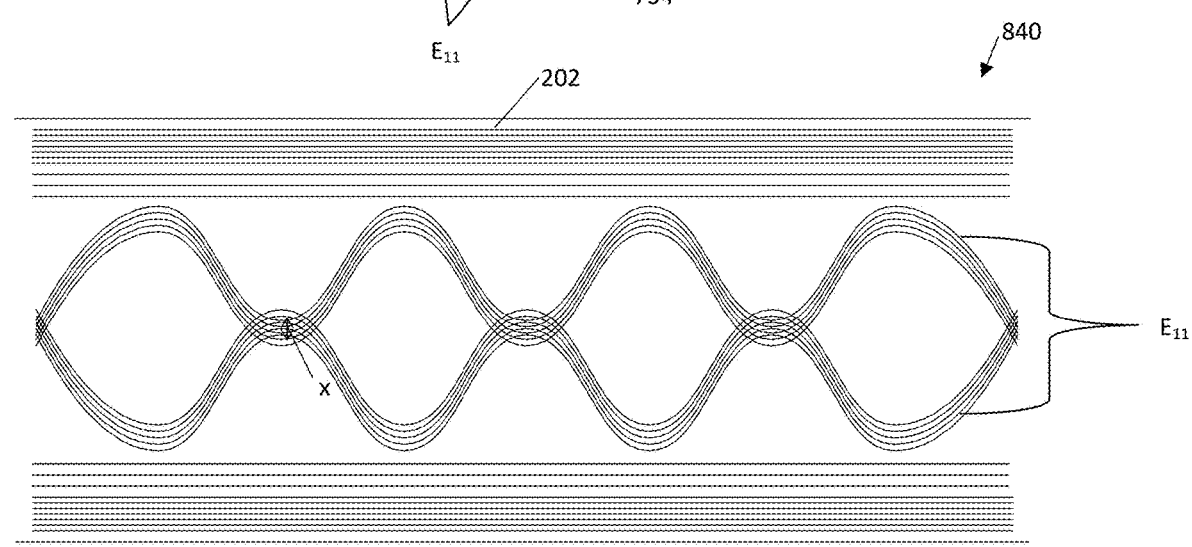
FIG. 8 is a simplified illustration of yet another alternative elastic composite web according to the present invention.
Figures 8A, 9:
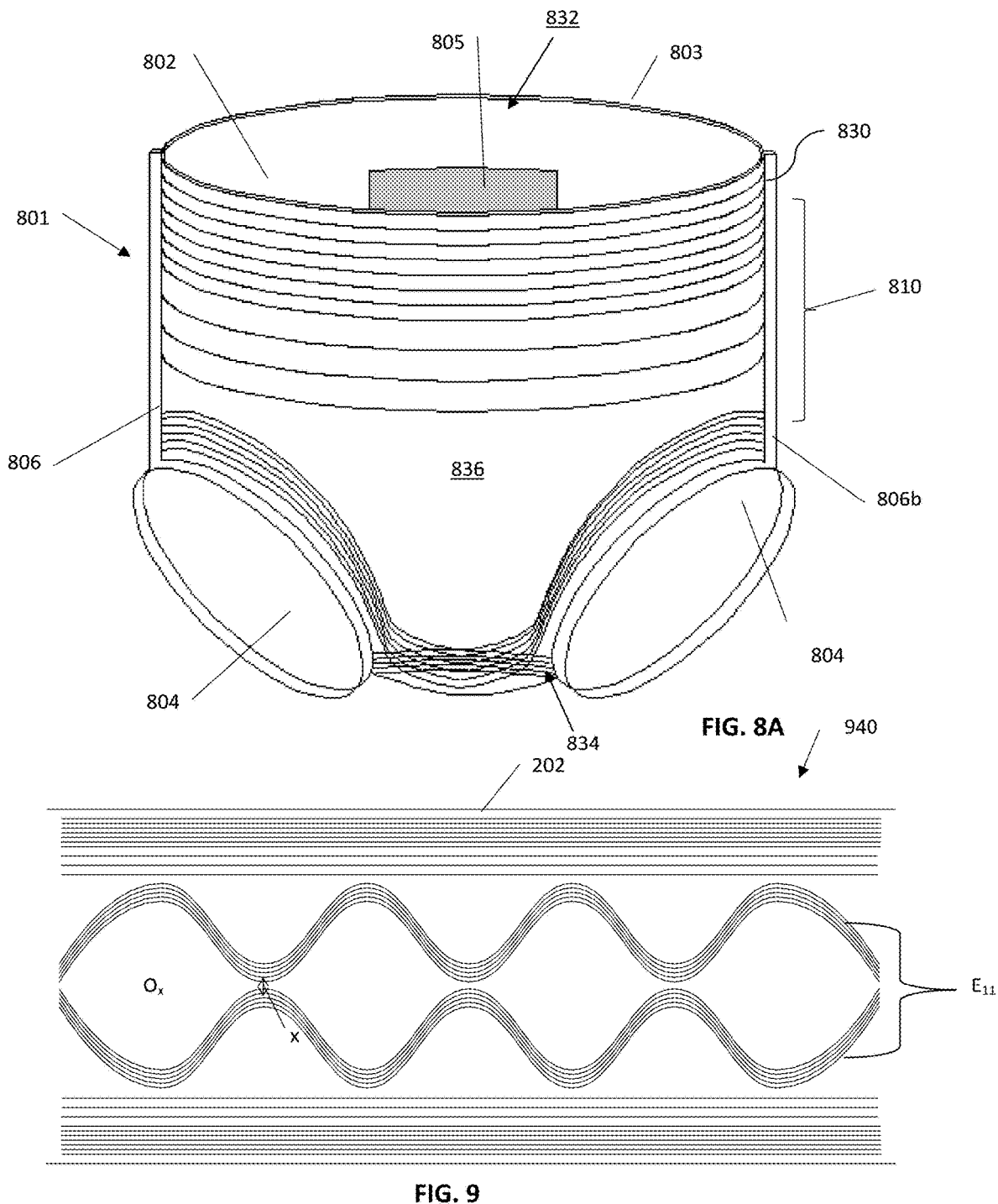
FIG. 8A is a simplified illustration in isometric view of another disposable absorbent article according to an alternative embodiment of the present invention.
FIG. 9 is a simplified illustration of yet another alternative elastic composite web according to the present invention.

FIGS. 7-9 illustrate further embodiments of the elastic composite webs and distribution that can be achieved by and/or utilized in the present invention, wherein like reference numerals are used to indicate like elements. Referring first to FIG. 7, the elastic composite web 740 includes an upper or backsheet material sheet (not shown) 712, a lower material sheet (not shown), but directly underlying the upper sheet 712 and multiple distributions of elastic strands. A distribution of elastic strands 710a, 710b is provided along each of the upper and lower edges 702, 703 of the web 740. These distributions ultimately make up the elastic annular region about the waist opening. Between these two distributions, two distributions 711a, 711b of variable elastics are provided (for the lower waist, crotch and leg regions). As in FIG. 3, these variably positioned elastic strands are distributed by means of the periodic, lateral motion of the elastic guides in FIG. 2, preferably to elicit a sinusoidal pattern. The first set 711a of elastics is distributed in a first sinusoidal pattern and are overlapped with the other set 711b of elastics distributed in a second sinusoidal pattern. In this exemplary embodiment, the first and second sinusoidal patterns are mirror images of each other. In this embodiment the degree of overlap "X" of the two elastic patterns is much smaller than that described in the embodiments relating to FIGS. 3 and 4. The resultant absorbent article made from this type of elastic distribution is described in FIG. 7, and features a greater amount of elastic material in the crotch region and less elastic material in a mid waist region.

FIG. 8 illustrates an alternate elastic composite web 840, wherein the degree of overlap or value of "X" is substantially zero or thereabout. An illustration of the absorbent article 801 utilizing this elastic distribution pattern and an elastic composite body 836 from severed from the web 840 is shown in FIG. 8A. The article 801 does not feature a crotch region 834 that is as broadly elasticized as that of the absorbent article 701 in FIG. 7.

Figure 9A:
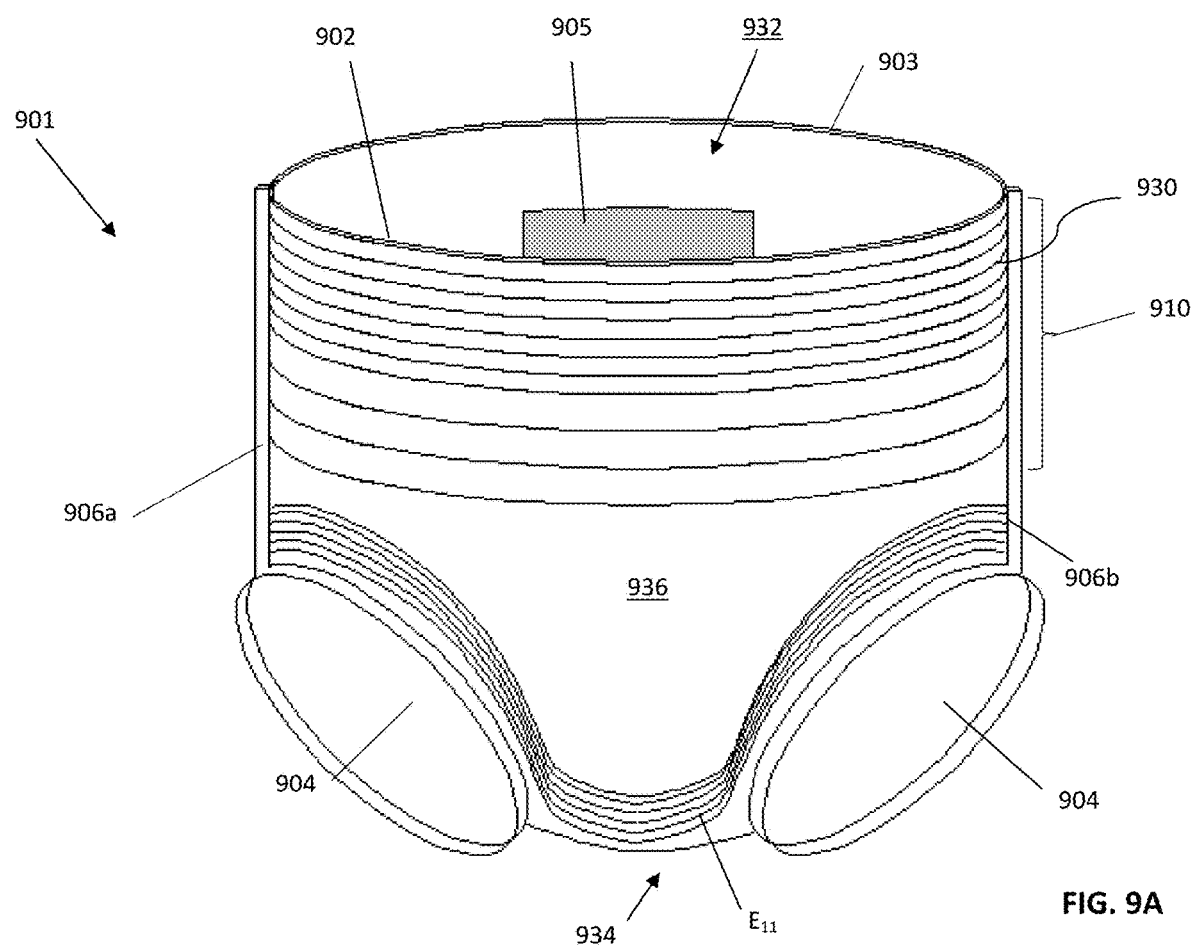
FIG. 9A is a simplified illustration in isometric view of another disposable absorbent article according to yet another alternative embodiment of the present invention.

FIG. 9 illustrates yet another, further embodiment of an elastic composite web 940 according to the present invention. This alternate composite web 940 employs an alternate variable distribution 911a, 911b of elastics. Specifically in this embodiment, the variable set 911a, 911b of elastic strands are distributed in a pattern in which the two sets do not overlap. In this example, the value of "X" is said to be negative. Although the patterns do not provide a series of completely annular elastic regions, the value of "X" is maintained sufficiently small so as to approximate a complete annular region, i.e., a substantially annular elastic region. An illustration of the absorbent article 901 utilizing such an elastic distribution and substantially annular elastic regions is illustrated in FIG. 9A. By being substantially annular, the elastics about the waist opening and leg opening occupy more than 85% to 95% of the complete circle, and thus, the elasticity about the opening is practically continuous and substantially complete.

Figure 11B:
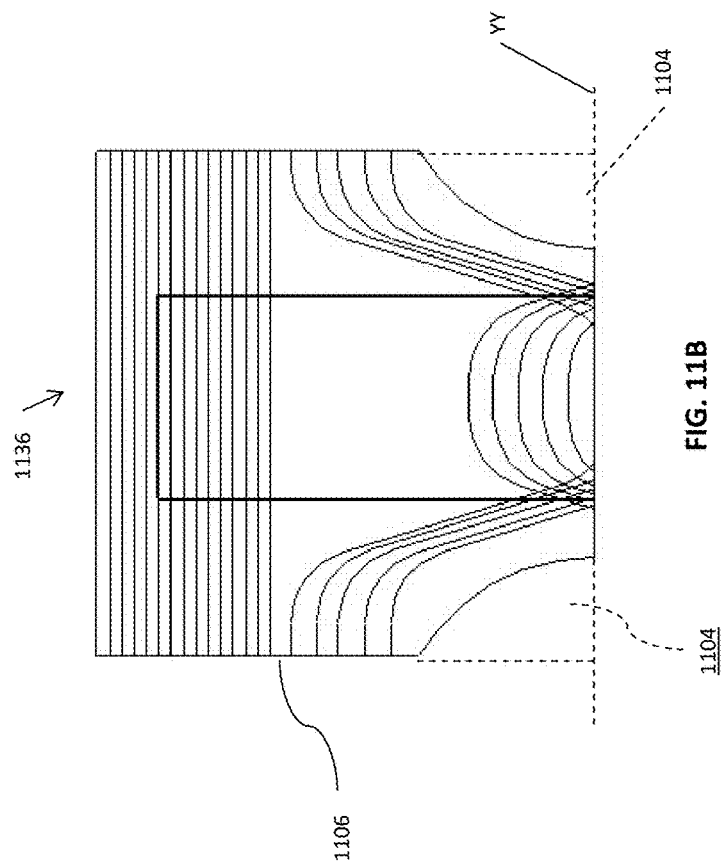
FIGS. 11A-11B are simplified illustrations of an elastic composite body, according to yet another alternative embodiment of the present invention.
Figure 11A:
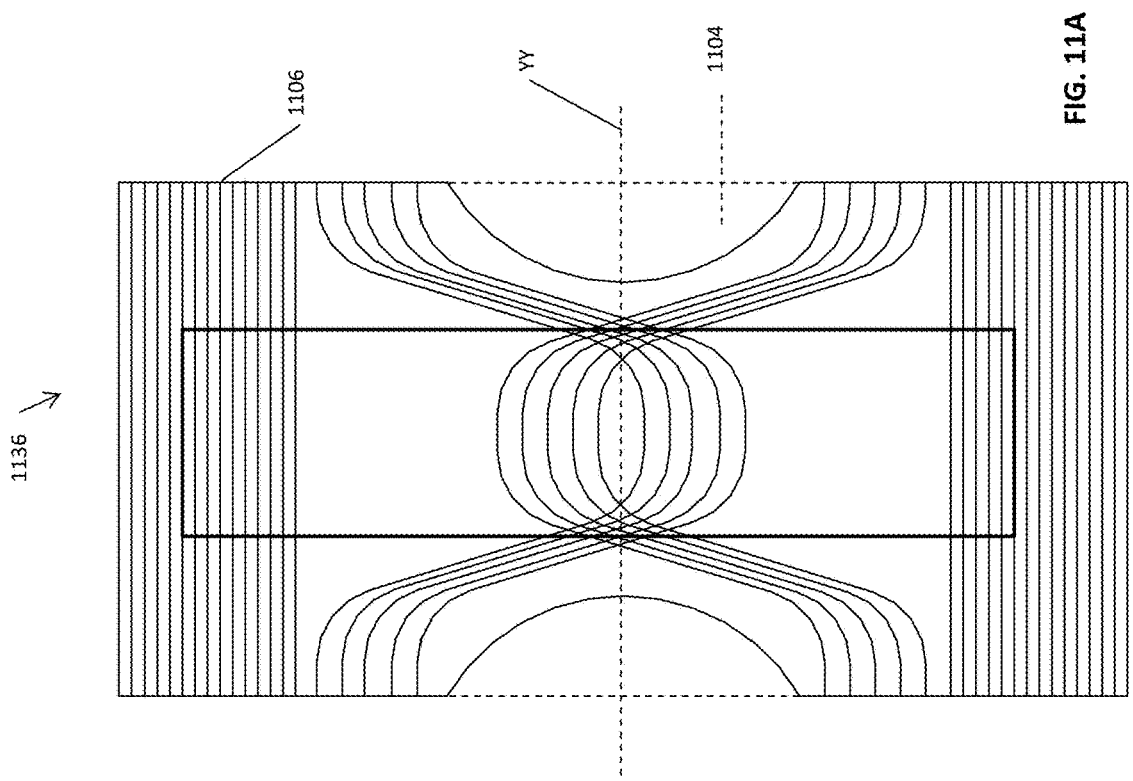

FIGS. 11A and 11B illustrate yet another elastic composite and disposable absorbent according to the present invention. The elastic composite is similar to that provided in FIGS. 8 and 8A. The overlap region dimension "X" has a value of zero, in that the two distributions 1111a, 1111b meet but do not completely cross. Instead, the two elastic distributions 1111a, 1111b form a broad, somewhat elongated concentration of elasticity at the center of the composite 1136. In the resulting disposable absorbent article, this feature translates to a concentration of all round elasticity in the crotch region 1134. FIGS. 11A and 11B are also provided to show exemplary dimensions of an elastic composite of the invention. The Figures also show preferred locations of certain element of the elastic composite 1136. For example, the core 1105 in this embodiment is located centrally over the concentration of elasticity discussed above, but is cut at a width that approximates the length of the elastic concentration discussed above.

FIGS. 11A and 11B also illustrate two stages in an alternative method of making a disposable absorbent article according to the invention. FIG. 11A reveals a unitary elastic composite body 1136 that could have been freshly severed from a web of elastic composite, according to the invention Unlike earlier described finished elastic composites, the elastic composite 1136 has not had holes or sections cut therefrom (for later-formed leg openings). Instead, the elastic composite 1136 is folded in its full rectangular frame about longitudinal axis YY. The folded elastic composite 1136 then features quarter sections of the leg holes 1104 that may be cut or stamped out. Thereafter, the side edges 1106 may be sealed to form the leg openings of the absorbent training pants, according to the invention.

Figure 12A:
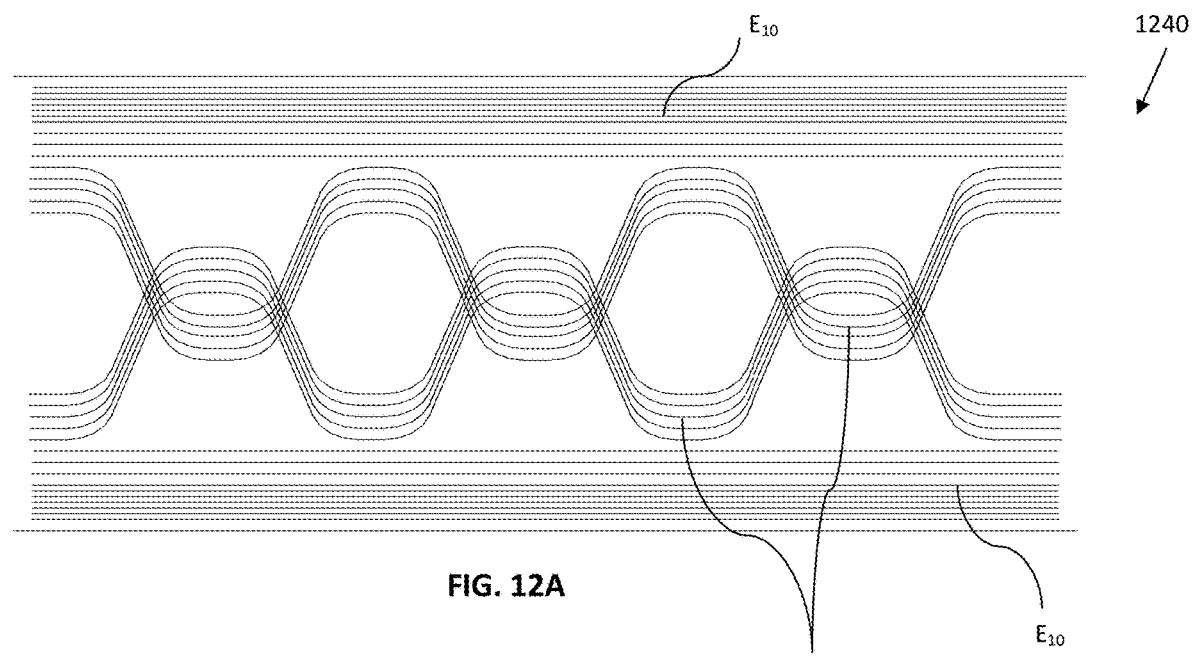
FIG. 12A is a simplified illustration of an elastic composite web having dual elastic distribution patterns applied thereon, according to an embodiment of the present invention.
Figure 12B:
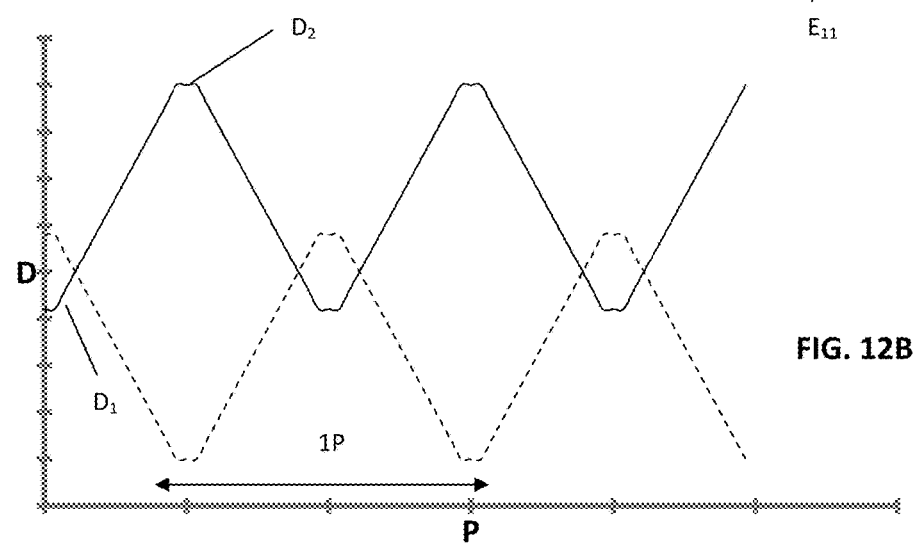
FIG. 12B is a graphical diagram of a periodic function reflecting directive lateral motion by elastic guides to produce the dual elastic distribution patterns on the elastic composite web of FIG. 12A.

In the illustration of FIG. 12A, another alternative elastic composite web 1240 is shown exhibiting a dual elastic distribution patterns (E10, E11). Among other things, the variable elastic distributions E11 feature a broader and more block-like shape to its large annular regions Ox', rather than the smoother, more rounded shape of earlier-depicted annular regions. FIG. 12B is a graphical diagram of a periodic function and pattern reflecting directive lateral motion by elastic guides to produce the variable elastic distribution patterns E11 on the elastic composite web of FIG. 12A. The graph reveals a relation characterized by a steep (almost abrupt) travel from a minimum displacement position (D1) to maximum displacement position (D2) over a half-period (½P), as well as the return to minimum displacement position (D1) over the second half-period (½P). This is reflected in the steep or abrupt angle of the elastic distribution E11 in FIG. 12A, as well as the necessarily tight concentration of the elastics during between the troughs and summits. The graph also reveals slight stall or levelling off of the elastic guide upon reaching the maximum or minimum displacement position. This feature is reflected by a somewhat flat area or plateau at each of the trough and summit of the elastics distributions E11. This pattern feature differs from the gradual, more rounded troughs or summits in earlier described elastic distribution patterns.

Accordingly, the absorbent article formed from an elastic composite of the web 1240 features a thinner, denser elastic annular region about the leg openings. Elasticity is more concentrated on the inside portion of the leg opening near and around the crotch region, as opposed to the area engaging the top of the thigh.

The flow chart 1300 of FIG. 13 illustrates an exemplary and preferred process of making the elasticized absorbent pants in FIG. 1. This preferred process corresponds substantially with the method of making the elastic composite which as described in respect to FIG. 5. The process commences with applying multiple distributions of elastics on a moving material sheet to form a moving web of an elastic composite (step 1361). Then, each of a core section and a second material sheet is periodically applied onto the moving web to define a finished web of discrete elastic composite bodies (steps 1362, 1363). In subsequent steps, discrete absorbent pants articles are shaped from the finished web. In the preferred shaping steps, a bottom half portion and a top half portion of the web and composite body are joined. More preferably, the elastic composite web is folded along a longitudinal centerline (step 1364). In this specific embodiment, a section of the folded web is periodically cut-out (step 1365), thereby periodically providing cut-out sections between core sections and in between elastic distributions. Next, the two half portions are sealed along or to create two laterally extending seal lines (step 1366), thereby preferably substantially joining multiple elastic distributions on one half portion with elastic distributions on the other half portion and creating a waist opening and pair of leg openings Finally, elasticized absorbent articles are separated from the web by severing the lateral side lines (step 1367). Most preferably, the sealing and severing steps immediately produce elastic absorbent pants having a waist opening, pair of leg openings, and multiple substantially continuous elastic distributions extending through two lateral seal lines and creating annular elastic regions about the waist opening and the leg openings.

The flow chart 1400 of FIG. 14 describes, more generally, the basic steps in a method of making an elastic composite web having multiple elastic distribution patterns thereon, according to the present invention. Such an elastic composite web is ultimately configured such that elastic composite bodies of absorbent pants may be separated from the web. The preferred method commences with the step of applying multiple continuous distributions of elastics on a moving web of material sheet to form a web of elastic composite moving in the longitudinal or machine direction, the distributions generally extending in the machine direction (Step 1461). The method further entails periodically applying a core section on the moving elastic composite web (step 1462). Then, a top material sheet is continuously applied on the web including the core sections (step 1463). In the step of applying continuous distributions of elastics, at least two periodic distributions of elastics are established on the moving web by varying the lateral position of the distribution of elastics as the distributions are advanced in the machine direction toward the moving web of elastic composite (sub-step 1461A). In further embodiments, the step of applying the continuous distributions may include periodically varying the lateral position of the elastic distribution prior to engagement with the material sheet and further yet, periodically varying the lateral position to establish two sinusoidal patterns on the moving web of elastic composite.

Asymmetric Leg Cutouts

Figure 4A:
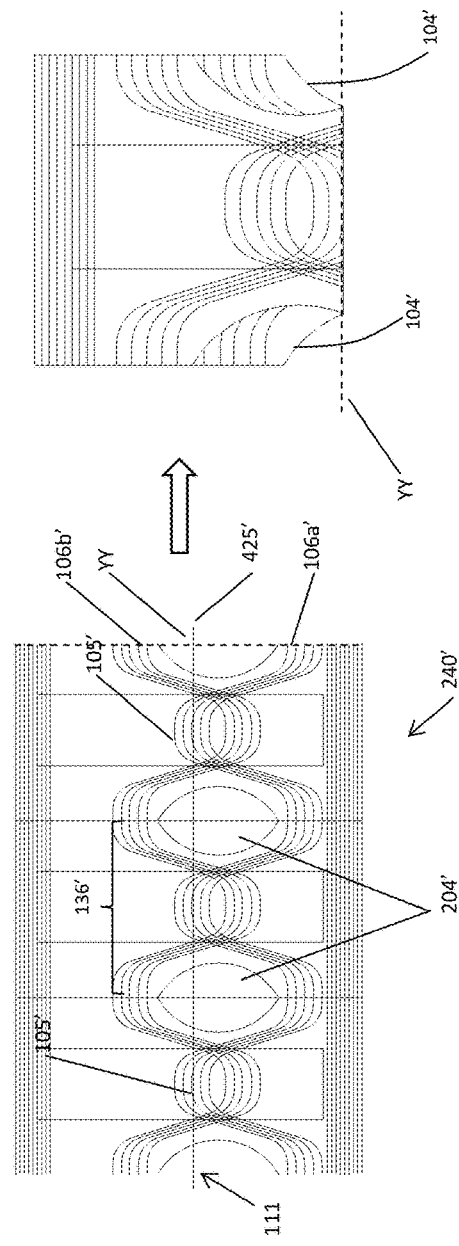
FIG. 4A is a simplified illustration of a web-based process for making an alternative disposable absorbent article, according to the present invention.

FIG. 4A is a simplified representation of a web-based process of making a disposable absorbent article 101' according to the present invention (wherein like elements are referred to using like reference numerals). A variation of the process described in respect to FIGS. 2-4, this process may be employed to produce a modified disposable absorbent article 101'. This alternate process is particularly suited to making an modified pants product 101' having fitted leg openings 104'. FIG. 4A shows the moving web 240' of elasticized composite bodies 136' from which a disposable absorbent article 101' is derived. As described previously, the leg openings 104' are formed subsequent to the folding step by joining two linear segments 106a', 106b' of the side edges of the elasticized composite body 136' and then sealing the union. The free non-linear cutout section (between the linear segments 106a', 106b') of the side edge substantially connect to form the leg openings 104'. In the finished absorbent pants product 101', each leg openings 104' may be described as having a front portion that is larger and extends further and arches higher than the back portion (e.g., as shown with the absorbent pants 101' in FIG. 4A). Thus, the front portion of the leg opening 104' rides higher on the thigh of the user than the back portion. In certain designs of the pants product 101', the asymmetric or uneven leg opening 104' enhances fit and comfort around the front thigh area of the user. This reduction in excess material on the front part of the pants, which is relatively flatter and less rounded than the back part when the pants are worn, allows for more room and discourages bunching and pinching on the front. The back portion of the leg hole fits lower and more snugly about the back of the wearer and, thus, preserves sealability and loading capacity in the back of the pants product.

As illustrated in FIG. 4A, the alternative pants product 101' is, in simplest terms, achieved by varying the leg hole cutout step. Specifically, holes 204' are punched out or otherwise cut into the web 240' at a position offset from the longitudinal centerline YY. With the circular cutouts in the previously described process, the cutouts are placed symmetrically about the longitudinal centerline YY and thus, about the fold line 425. For the exemplary pants product 101', a circular or ellipitical cutout 204' is placed asymmetrically about the longitudinal centerline YY and lower relative to the longitudinal centerline. In FIG. 4A, the cutouts 204' provide an arc region below the longitudinal axis YY that is larger (in arc length and area) than the arc region provided above the longitudinal centerline YY. In the folding step, the web composite 240' is folded along the fold line 425, which corresponds to the longitudinal centerline YY, to form the leg opening 104'. As a result, the front part of the leg hole 104' is roomier and rides higher on the thigh of the wearer.

As with the previously described embodiments, periodic elastic distributions of elastic are directed about the leg cutouts 204' and leg openings 104'. The elastic distributions 111' form elastic annular regions about the leg holes 104', thereby enhancing fit and support. In this particular embodiment, the elastic distributions 111' that closely traverse the top of the leg cutouts exhibit a flatter pattern than the other elastic distribution.

In another variation, the leg cutout may be employed in a shape other than a circle. For example, an elliptical cutout may be employed to form a leg opening in the pants product that is sleeker or narrower than that resulting from a circular cutout. In either variation, a curvilinear elastic distribution may be applied to accommodate the leg cutouts and ultimately, provide an annular elastic region about each leg opening in finished pants product. The inventive method of elasticizing a moving web substrate is, therefore, shown to be well suited for providing annular elastic regions about leg openings of different shapes and locations on the web.

Shorts-Like Elasticized Pants Product

Figure 15A:
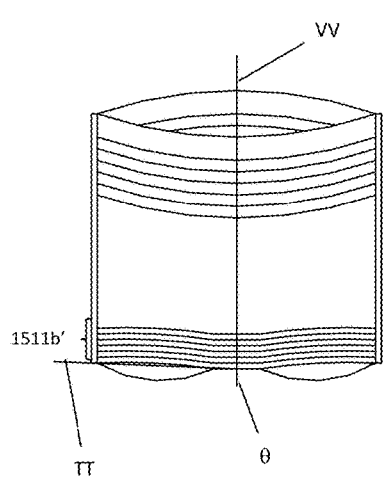
FIG. 15A is a simplified illustration in isometric view of a disposable absorbent article according to an alternative embodiment of the present invention.
Figure 15B:
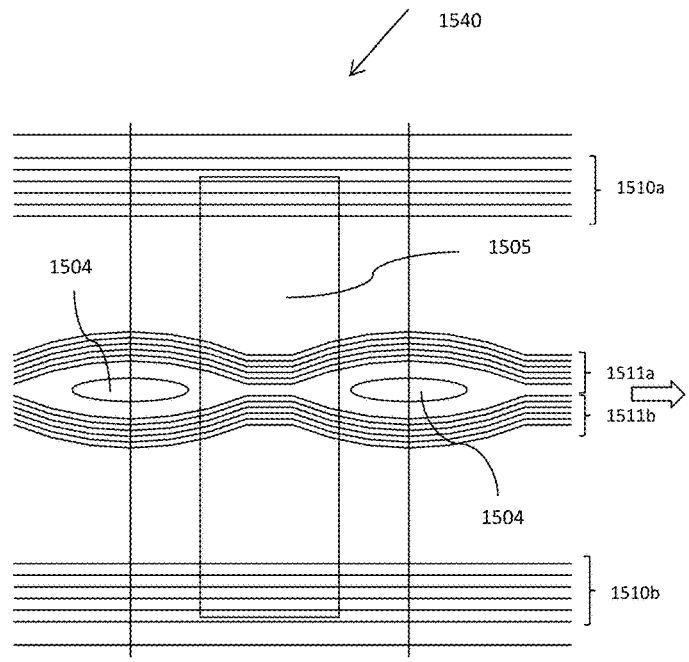
FIG. 15B is a simplified illustration of a web of elasticized composite bodies from which the article in FIG. 15A is derived.
Figure 16A:
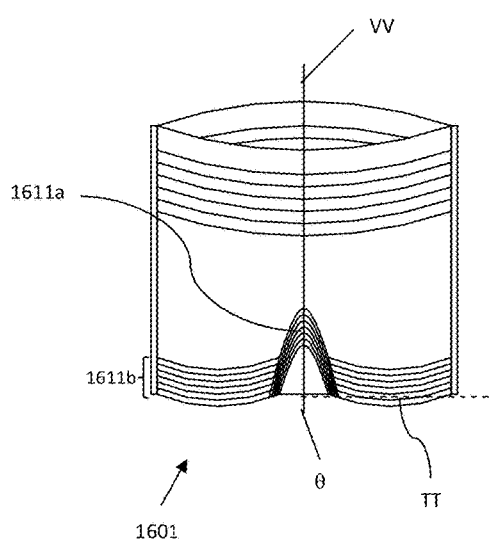
FIG. 16A is a simplified illustration in isometric view of a disposable absorbent article according to an alternative embodiment of the present invention.

With reference to FIGS. 15A-15B and 16A-16B, a variation in the previously described method of making an absorbent pants product according to the invention will now be discussed. In this embodiment, the steps of applying distributions of elastics and providing leg cutouts in a moving web 1540 are modified to produce an alternative or modified pants product 1501. Two exemplary pants products 1501, 1601 are depicted in FIGS. 15A and 16A. The pants products feature a flatter or more horizontal leg opening 1504, 1604, which may be described by a leg opening angle θ between the vertical centerline VV of the pants and a plane TT tangent to the leg opening. As compared to the previously described pants products, the leg opening angle θ in these embodiments are rotated outward and closer to 90 degrees. In the pants product of FIG. 1, the angle θ is close to about 45 degrees, whereas each of the pants product of FIGS. 15A and 16A features a leg opening angle that may be greater than about 75 to 80 degrees.

The simplified illustration of a moving web substrate in FIG. 15B shows the modifications to the elastic distributions 1511a, 1511b and the leg cutouts 1504 required in a process of making the pants product 1501. Firstly, the leg cutouts 1504 are not circular but are in the shape of relatively flat ellipticals. The short diameter of the elliptical is substantially less than the long diameter, creating a cutout 1504 that is more slit-like than a circular hole. Secondly, the elastic distributions 1511a, 1511b provided about the leg cutout 1504 is flatter and less sinusoidal. In this exemplary embodiment, the two elastic distributions 1511a, 1511b do not cross or overlap. The upper distribution of elastics 1511a stays above the longitudinal centerline YY and the lower elastic distributions 1511b is maintained below. The elastic distributions 1511a, 1511b are not completely flat, but feature a slight curvature while traversing the periphery of the leg cutout 1504. In any event, an annular elastic region about the leg opening 1504 is achieved.

Figure 16B:
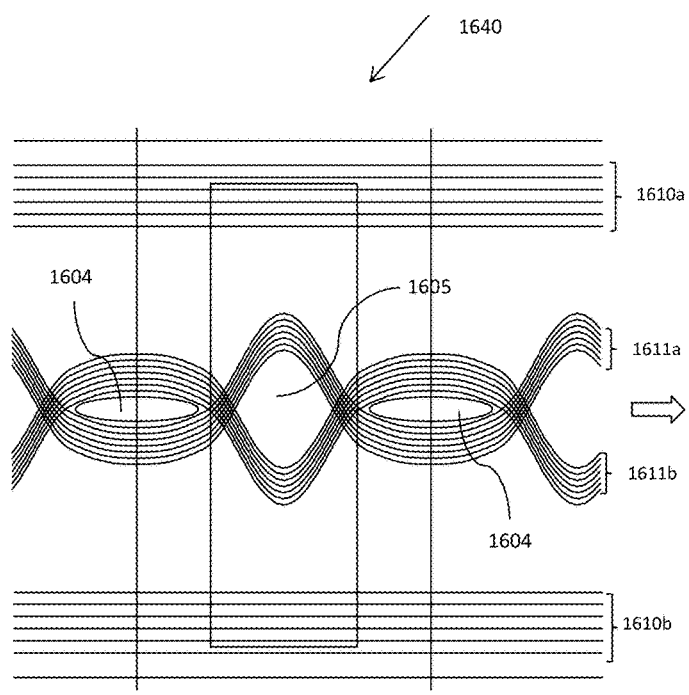
FIG. 16B is a simplified illustration of a web of elasticized composite bodies from which the article in FIG. 16A is derived.

Now referring to the simplified illustration of a moving web 1640 in FIG. 16B, the two sets of elastic distributions 1611a, 1611b intersect to create a more sinusoidal pattern around the area of the core 1605 or at least, a periodic pattern featuring alternating sections of high amplitude and low amplitude. In the area where the leg cutout 1604 is to be provided, however, the distribution of elastics is flatter and closely follows the elliptical slits 1604 in the web 1640. The intended crotch regions of the web 1640 are traversed by a pair of elastic distributions 1611a, 1611b of high amplitude. The elastics pass over and are concentrated on the upper extent and the lower extent of each elongated core placement. In this way, the elastics generally proximate the outside periphery of the core 1605.

In either pants product, the resultant leg opening is described as being substantially circumferentially elasticized and featuring an elastic annular region. When worn, the annular elastic region substantially encircles the thigh of the user. In one respect, the pants product of FIGS. 15A and 16A are attributed with characteristics more akin to elasticated shorts (e.g., bike shorts). In this way, the pants product is provided with an encircling elasticized support about the thigh of the user. This circumferential support is generally more horizontal and focused lower than that of the leg hole of the pants product 101 in FIG. 1A. The circumferential engagement between each elasticized leg opening and the thigh of the wearer serves as an anchor point for the absorbent pants product. Together with the circumferential elastic annular region about the waist, the elastic annular regions around the leg opening actively seal the pants product about the body of the wearer. Importantly, support provided by the elasticized leg holes also provides enhanced support in the crotch region and core area of the pants product.

Gapping in the Elastic Distributions

In yet another aspect of the present invention, the system and method of making an elasticized absorbent product includes a modified step of applying multiple distributions of elastics on the moving web. As described previously, in a preferred process, continuous distributions of elastics are applied generally in the machine direction. This includes applying and establishing at least two periodic or curvilinear distributions (generally in the machine direction) of elastics on the moving web by varying the lateral position of the elastics as the elastic distributions are advanced in the machine direction. Further to this step, continuous distributions of elastics may be applied to establish generally machine-directed distributions of elastic on each elastic composite body which have intermittent gaps (in the elastics). That is, a continuous, generally machine-directed distribution of elastic is applied, but the elastic strand on the finished composite web and on the final product is effectively segmented due to the intermittent gaps.

The locations of the gaps on the web are predetermined to correspond with desired gaps or absence of elastics in the final pants product. In some applications, the gap may be sufficiently wide to effectively de-elasticize the target area and in other applications, will be minimized to maintain continuity in the annular regions of elasticity in the final absorbent product. In one exemplary process, gaps in the elastic distributions are provided at locations on the web that correspond to the side edges of the pants product, whereupon the side seal or seams are formed. In yet another embodiment, gaps in the elastic distributions are located to coincide with the core location near the central or crotch region of the absorbent article. In this embodiment, it may be desired to disengage the core from the elastics and provide a relatively stable and unbiased core structure, or allow undisturbed placement of additional elements onto the core surfaces.

Figure 17:
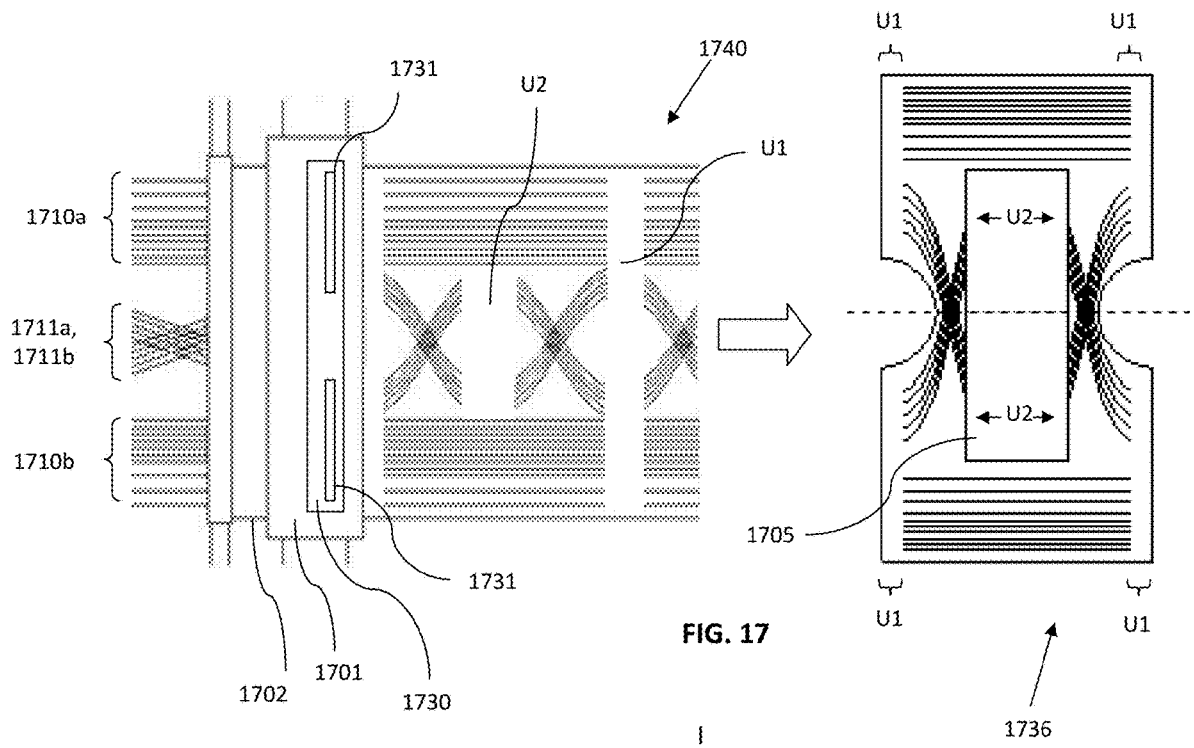
FIG. 17 is a simplified illustration of a system and process of applying elastic distributions on a web of elastic composite bodies, according to the present invention.

To exemplify these variations in the process and in the absorbent product of the invention, FIG. 17 provides a simplified illustration corresponding to the illustrations of FIGS. 2A-B and 4, with an elastic cutting or gapping step incorporated into the process. FIG. 17 shows the web 1740 of elastic composite delivered by rollers 1701 and 1702 and an elastic composite body 1736 severed from the web 1740. As shown in the moving elastic composite web 1740, multiple continuous distributions of elastics 1710a, 1710b, 1711a, 1711b are applied on the moving web with the two middle periodic elastic distributions 1711a, 1711b overlapping along the central portion of the web 1740. In this embodiment of the invention, the absorbent product 1701 is provided with gaps U1 along the proximity of the side edges or seams. The removal of elastics in this area provides a flat and consistent surface that may better accommodate a sealing operation, such as ultrasonic bonding or heat treatment. Furthermore, the flatter and more consistent surface, without shirring, may be deemed more aesthetically appealing in some product designs. In some applications, the gaps U1 will be minimized to ensure continuity of the annular elastic regions discussed previously.

As described previously, the distributions of elastics 1710a, 1710b, 1711a, 1711b may be applied on a nonwoven web of backsheet material as both input feeds engage a form roller 1701. Then, a web of intermediate nonwoven meets the form roller 1701 and is applied over the elastics to form a subsequent web featuring multiple continuous distributions of elastics sandwiched between two nonwoven webs. Preferably, the elastics are subsequently cut or gapped by engagement of the form roller 1701 with a cutter roller 1730, and while retained in this sandwich and before the elasticized web meets the input feed of core section(s). Such lamination of the elastics helps to hold the elastics in place during and after cutting. In this technique, the elastics may be severed by pressing a blade of the cutter roller 1730 through the intermediate nonwoven layer and against the roller 1701, preferably with minimal puncture of the backsheet layer.

In one suitable arrangement, the form roller 1701 engages a second roller 1730 equipped with a set of blades or cutters 1731 for cutting the elastics, as known in the art. One suitable arrangement may be found in the specification of U.S. Pat. No. 4,525,229 (see e.g., FIG. 2). For the exemplary pants product design, a first pair of blades or cutters 1731 is spaced axially apart and has a lateral width sufficient to engage the extent of waist elastics. The cutters 1731 are, therefore, positioned near the ends of the cutter roller so as to correspond to the lateral locations of the waist elastic distributions on the web. In the depicted embodiment, the cutters 1731 are sufficiently axially long to reach and sever the middle elastic distributions 1711a, 1711 as well as waist elastics 1710a, 1710b. In further embodiments, two independent pairs of cutters may be employed, however, to minimize puncture of the nonwoven layers. A second pair of similarly spaced apart cutters (not shown) is provided just several degrees from the first pair of cutters 1731. The spacing between the two pairs is selected to correspond to the desired gap U1 on the moving web 1740 and to proximate the width (actually twice the width) of the desired side seam.

As known in the art, the speed of the cutter roller 1730 is synchronized with the rotation of the form roller 1701 so as to properly articulate the required gapping. The cutters 1731 may further register with an anvil(s) provided on the form roller 1701 to make the desired cuts. In the depicted embodiment, the circumference of the form roller 1701 may correspond to four or five times the width of one pants product on the web 1740. Thus, the form roller 1701 is equipped with a number of properly spaced anvils, and the cutter roller 1730 will rotate at a rate that causes the cutters 1731 to engage the anvils.

In yet a further embodiment, the pants product may be freed of elastics in and around the location of the core 1705. A desired gap U2 has a width that approximates the width of the core 1705. Such a modification may be desired to provide stability and consistency to the core, including preventing any bunching of the core as well as the adjacent nonwoven sheet(s). In this particular design, only the two middle distributions of elastics 1711a, 1711b are gapped, as the waist elastics 1710a, 1710b do not encroach upon the intended area of the core 1705. The same roller 1730 as the one cutting the waist elastics, or another cutter roller, may be provided to engage the form roller 1701 and place intermittent gaps U2 in the two sets 1711a, 1711b of periodic or curvilinear elastic distributions. As the target distributions of elastics are typically closer to the center of the moving web, the cutters and matching anvils are also located near the center of the cutter roller 1730 and form roller 1701, respectively. To make the desired cut, two pairs of axially spaced apart cutters may be used or one longer cutter that extends from one elastic distribution to the other. Preferably, two successive pairs of cutters are provided that are spaced part in correspondence with the gap in the elastics.

Elasticized or Profiled Core Structures

In the systems depicted in each of FIGS. 2 and 6, as well as that described in respect to the process illustrated through FIGS. 3, 4 and 5, the core is delivered intermittently to the moving web pre-cut and oriented generally perpendicularly to the longitudinally moving direction of the moving web. As specifically shown in each of FIGS. 4 and 5, the pre-cut core is delivered on the web extending lengthwise between the longitudinal edges of the web, but in between each side edge (or severing line) of the elasticized composite. The core is, therefore, deposited in correspondence with its final location and orientation in the finished disposable absorbent product.

Figure 18:
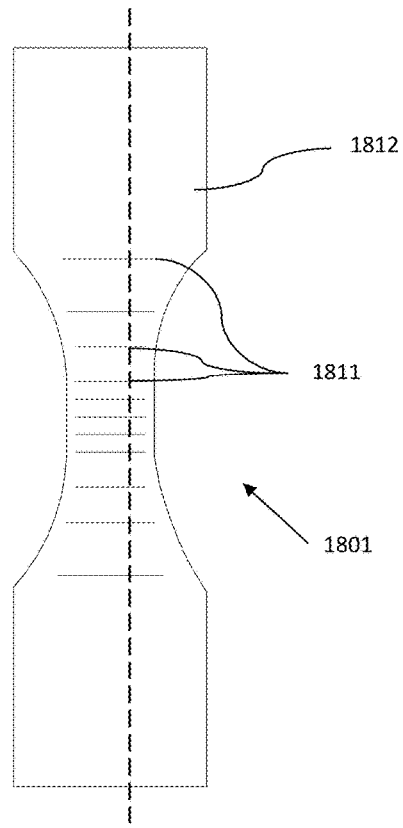
FIG. 18 is a simplified illustration of an elasticized core structure achievable by the system and process according to the present invention.

In many of the embodiments described herein, the inventive process is employed to apply a distribution of elastics across the width of each absorbent product, including over the core. The engagement or interaction between the elastics and the core may impart elasticity to the core, as required or desired by the design of the absorbent product. The resulting elasticized core may feature aesthetic and functional characteristics due to its elasticized regions. The benefits of elasticized core configurations have been discussed, for example, in U.S. Patent Application Publication No. US2011/0130736 A1, specifically FIGS. 6-9 in that publication (which application is assigned to an Assignee common with the Assignee of the present application and include, as inventors, one or more of the inventors named for the present application). One of the Figures is reproduced herein as FIG. 18 to illustrate an elasticated core structure 1801 (in a contracted state) achievable with the present inventive system and process. The core configuration includes a plurality of elastic distribution 1810 applied laterally in machine direction, and generally centrally on the moving web and across the core 1812. This previous patent application publication and specifically FIGS. 6-9 of the publication, and the descriptions accompanying those Figures, are incorporated herein for background purposes and made a part of the present disclosure. The common element in these referenced elasticized core designs is that elastics 1811 are directed and applied onto or proximate the core 1812 in the direction lateral to the lengthwise direction of the core 1812. In the present system and process, the application of elastics in the machine direction and centrally on the moving web, and the intermittent deposition of the core onto the web substrate in its ultimate position and orientation facilitate the provision of such an elasticized core. Moreover, the presently described system and process allow for variations in the elastic pattern applied to the core, including a plurality of different distributions or sets of elastics, spacing between the elastics, linear and/or curvilinear distribution patterns, including sinusoidal and other shapes.

The present system and process also allows for the cutting or gapping of the elastic distributions on the moving web and in the finished disposable absorbent product. In one embodiment, other curvilinear or periodic designs may be employed to distribute elastics about and proximate the periphery of the core and to encourage a pocket or cup shape in the core. The overlap of the two elastic distributions creates an annular elastic region along the periphery of the core, which can advantageously act as a type of O-ring seal. Such an elasticized O-ring may be designed in alignment with the user's bottom to improve absorption and retention. The elastic distribution shown in FIGS. 3-4 and 7-7A are two configurations suited for establishing such an annular elastic region and o-ring seal about the area of the core.

Several further variations in the process may be employed to engage the elastic distributions with the core. As discussed above, the elastic may not be applied directly to the core. For example, the elastic may be applied to the backsheet and situated between the backsheet and a second sheet or nonwoven. The resultant composite is then bonded with the core. With this composite, and specifically the backsheet directly engaging and connected with the core, the elastics within the backsheet composite act upon the core to create the desired elasticized and/or profiled shape. In another exemplary variation, the elastic may be applied to the backsheet and then the core is applied directly on top of the elastics (e.g., without an intermediate sheet). In any case, the elastic and sheet materials, and the core, are brought together on the form roller, and adhesive may be applied to the material sheets and elastics just before arrival at the forming roller.

In several of the core designs of FIGS. 6 and 7 in the referenced U.S. Patent Application Publication No. US2011/ 0130736 A1, the elastics are applied laterally and centrally on a rectangular core or in specific embodiments, in both or each of two overlapping cores. Elastication of the absorbent core structure, upon release of tension in the elastics, creates a narrowed central region of the elasticized core, which, as described in the referenced publication provides aesthetic and functional benefits in the absorbent product. In further embodiments, the spacing or pitch between successive elastics may be designed so as to create more of a concave narrowed central region. This may be achieved, for example, by placing a higher concentration of elastics along the center and a lower concentration away from the center (see e.g., FIGS. 7C-D in the referenced publication). The elastics may be strategically placed between a stack of cores and other materials to provide the profiled core configurations in FIG. 8 (of the referenced publication) as well as the corrugated configuration of FIG. 9 (in the referenced publication).

Elastic Composite Web Forming Mill

Figure 10:
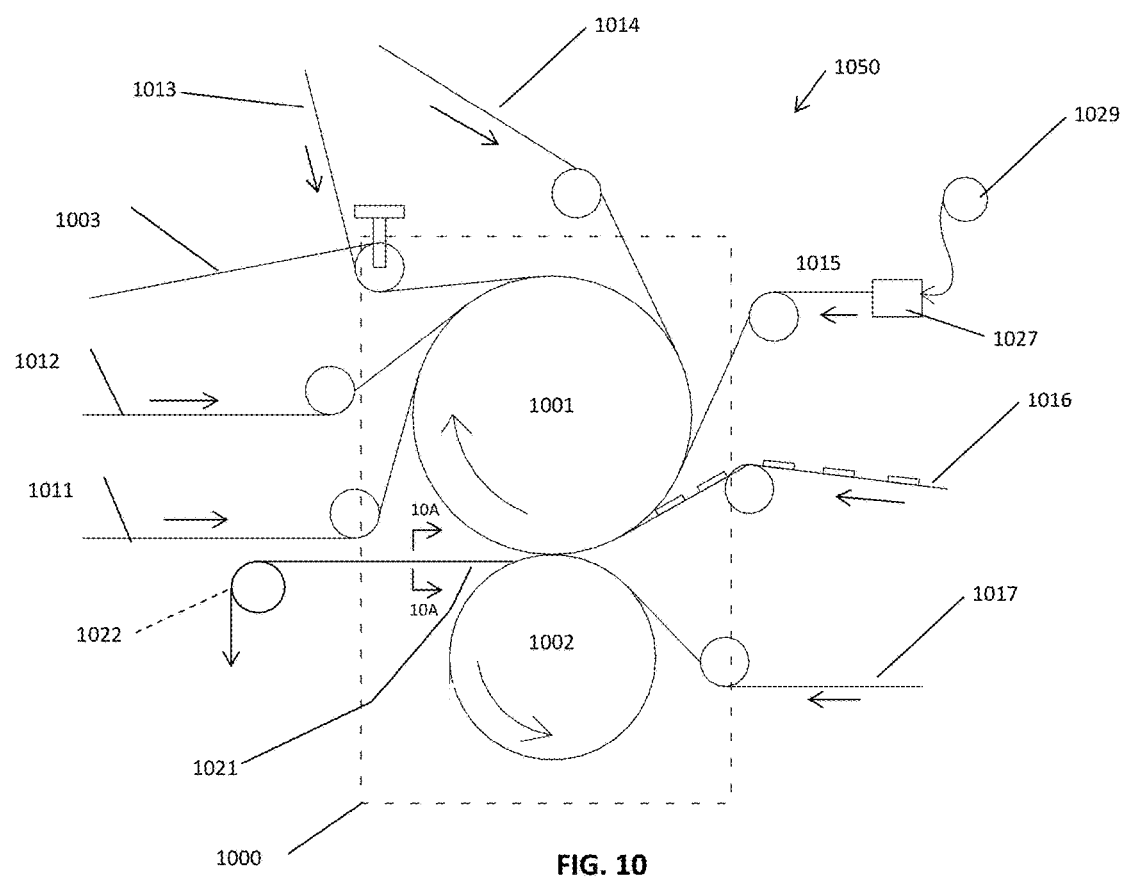
FIG. 10 is a simplified schematic representation of a system for making a disposable absorbent article according to the present invention.

FIG. 10 is provided as a simplified physical representation of a system 1050 according to the invention, and more specifically, an elastic composite web forming or joining mill 1000 of the system. The area (or region) inside the dashed box represents, in one aspect of the inventive system 1050, a centralized conglomeration of web components and system machine components, from which the desired web 1021 of discrete elastic composite bodies are outputted. The inventive system 1050 may be described as comprising a plurality of feed lines that converge on the joining mill 1000 in a predetermined manner to produce the predetermined moving web substrate 1021. The input feed lines are managed to direct a component of the product at a rate, speed, orientation, and lateral placement required of the web substrate product. Some input feed lines may be associated with "cut and place" units that intermittently apply a discrete unit of material to the moving web. Furthermore, the input feed lines are managed to converge and engage other input feed lines in the desired sequence and rate required.

With the system 1050 in FIG. 10, each of the elements of the web substrate is preferably applied to the mill 1000 linearly or inline in the machine direction. Accordingly, all feed lines and output lines can approach the mill 1000 from the right or left, or the top of the mill 1000, but within a lateral window not exceeding the axial length of the form roller 1001 (and, in some micro-applications, not substantially wider than the width of the web substrate 1021a). This physical characteristic of the system 1050 promotes manageability and flexibility in the process, including the ability to modify the properties of the finished absorbent product. The inventive system, and more particularly the mill 1000, also displays a small footprint. The mill 1000 also lends itself to being packaged as a modular, self-contained unit.

Figure 10A:
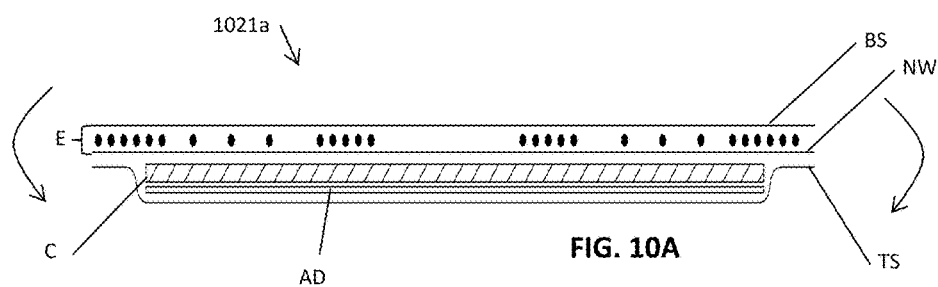
FIG. 10A is a cross-sectional view of a web of elastic composite bodies according to the present invention.

In one embodiment of the invention, a web substrate product 1021a is outputted by the mill 1000 as shown in the lateral cross section of FIG. 10A. Upon output from the mill 1000, the moving web substrate 1021a comprises a layer of topsheet TS on the bottom, an AD (acquisition and distribution) layer above the topsheet TS, and a series of individual, elongated cores C above the AD layer AD. Above this, a sandwich is provided of an intermediate nonwoven layer NW, a layer of backsheet BS, and various elastic distributions E therebetween. Directional arrows in FIG. 10 indicate the direction toward which the composite web 1021a is folded. As shown, the web 1021a is folded such that the topsheet layer TS rotates toward itself and is ultimately positioned on the inside of the folded web. In the finished absorbent article as worn, the topsheet TS is placed adjacent the body of the wearer.

After emerging from the mill 1000, the web substrate 1021a may be folded, sealed, and cut to produce the disposable absorbent article. These subsequent steps are considered post-joining steps that are implemented after delivery or output of the web 1021a. The folding step is performed at a folding station 1022 comprising of angular directional bars that are located immediately forward of rollers 1001, 1002. The folding station 1022 directs the web 1021 to a series of turns that flips and folds the substrate 1021a. Once folded, the leg holes are cut out, the side seams are sealed together, and then, the web substrate is severed along the seams (to produce discrete pants products). These steps have been discussed in respect to FIGS. 4 and 5, for example. Additional, pre-packaging steps may also be employed after the sealing and severing steps. In alternative embodiments, the step of cutting or punching the leg cutouts may be provided before the folding station 1022 and immediately after delivery of the web substrate output 1021a.

It should be noted that the post-joining steps may be modified so as to provide for a diaper product, as opposed to a pants product. In such a variation, the side seam sealing step may be eliminated. In this respect, the web substrate output may only require the severing step to product discrete diaper products. In a further variation of the system, process, and product that is derived from the inventive system and process, the web substrate outputted by the joining mill may be folded in the reverse direction to produce a modified pants product or diaper. Such a product objective may require modifications to the input feed lines to the joining mill, as further described below.

Referring now to FIG. 10 and well as FIG. 10A, several stages of the joining process are described as a sequence of joining various components of the web substrate 1021a. The primary components of the mill are a main or forming roller 1001 and a corresponding secondary roller 1002. As shown in FIG. 10, an input feed 1011 of backsheet material is engaged by the forming roller 1001 as well as the distributions 1012 of waist elastics and distributions 1001, 1003 of curvilinear elastics (as previously described in more detail in respect to FIGS. 2A and 2B). The moving web of elastics applied to the backsheet is then engaged from above by an input feed 1014 of intermediate nonwoven. This engagement sandwiches the elastics within the backsheet and intermediate nonwoven. In further embodiments, a cutter roller may be added to engage the form roller and to selectively cut one or more of the elastic distributions sandwiched by the backsheet and intermediate nonwoven.

The resultant elasticized web then engages the input feed 1016 of spaced apart and laterally oriented cores. As described previously, the cores are spaced in correspondence with a central position on the final pants product and in alignment with the longitudinal centerline of the moving webs and the forming roller 1001. The cores are preferably delivered pre-cut in an elongated rectangular form that is lengthwise to the longitudinal or machine direction. A cutting roller machine 1027 is provided upstream of the rollers 1001, 1002 and receives a continuous feed of sheet core material from a supply roll 1029. Preferably, a second input feed 1016 of a second core or an ADL layer is directed atop and upon the resultant elasticized composite (with core). In this instance, an input feed 1017 of the topsheet engages the elastic composite (with cores) to provide a topsheet layer over the core material(s). The resultant product is a moving web substrate 1021 of an elasticized absorbent composite that may be further processed to produce a pants product or a diaper product.

In this system configuration, the web substrate 1021a is delivered with the backsheet BS on top and the topsheet TS on the bottom. The continuous web 1021a is the preferably passed to the folding station 1022, which effectively flips and folds the web 1021a. From there, the side seams of the web 1021a may be sealed and then severed, to produce discrete elastic composite bodies.

Reversed Elastic Composite

Figure 10B:
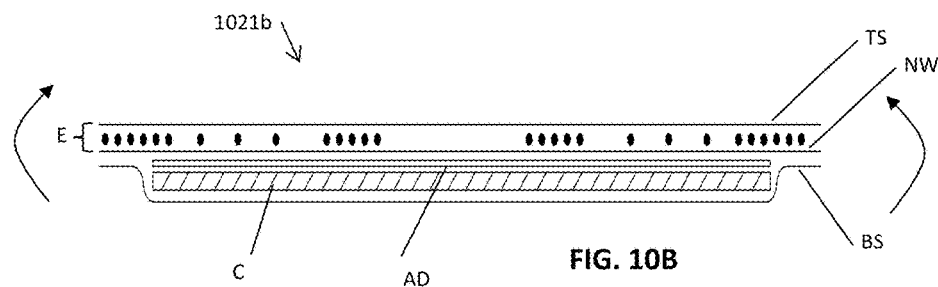
FIG. 10B is a cross-sectional view of an alternative web of elastic composite bodies according to the present invention.

In a further embodiment, an alternative disposable absorbent product is produced by the system and process by modifying the input feed lines to the joining mill 1000. Such an alternative moving web substrate 1021b of elasticized composite bodies is depicted in FIG. 10B in lateral cross-section. The moving web 1021b outputted by the joining mill 1021 provides a topsheet layer TS as a top layer and multiple distributions of elastics E sandwiched between the topsheet layer TS and an intermediate nonwoven layer NW. The core C, the ADL layer AD, and the backsheet layer BS fill out the rest of the elastic composite. Referring to FIG. 10, such a composite web 1021b may be achieved by switching, for example, the topsheet feed 1017 with a backsheet source and perhaps, as necessary switching the ADL and core input feed sources. Finally, the resultant web substrate is folded in the reverse direction (see fold directional arrows) such that the elastic distributions E are inside of the core C. By placing the elastics closer to the user, the topsheet TS is drawn closer to and about the body of the wearer and the elasticized composite 1021b will tend to support and accommodate the contour of the wearer's body. The improved engagement of the topsheet TS about the wearer not only enhances fit, but the topsheet TS is better positioned to prevent leakage. In further embodiments, the inventive process may be employed to apply sinusoidal or other curvilinear elastic distributions about the periphery of the core, thereby creating an elastized pocket about the topsheet/intermediate nonwoven sub-composite or the core. The incorporation of such an upwardly biased pocket may also be conducive to the use of one or more central apertures for disposal into the space between the core and the topsheet/intermediate nonwoven.

The foregoing description of the present invention has been presented for purposes of illustration and description. It is to be noted that the description is not intended to limit the invention to the various articles, products, systems, apparatus, and processes disclosed herein. Various aspects of the invention as described above may be applicable to other types of disposable absorbent articles and garments, and processes for making the same. For example, the elastic composite described above, may be incorporated in other disposable absorbent garments such as diapers, etc. or in other areas or as other components of the garment. Moreover, the processes described by FIGS. 1-18 may be utilized to produce compositions, garments and articles other than those described herein. Such variations of the invention will become apparent to one skilled in the relevant consumer products are provided with the present disclosure. Consequently, variations and modifications commensurate with the above teachings, and the skill and knowledge of the relevant art, are within the scope of the present invention. The embodiments described and illustrated herein are further intended to explain the best modes for practicing the invention, and to enable others skilled in the art to utilize the invention and other embodiments and with various modifications required by the particular applications or uses of the present invention.

What is claimed is:

1. A disposable absorbent article comprising:
a topsheet layer;
a backsheet layer;
multiple distributions of elastics disposed between the topsheet layer and the backsheet layer; and
a core disposed between the toposheet layer and the backsheet layer;
wherein the multiple distributions of elastics include at least two curvilinear distributions of elastics that include a first periodic elastic distribution and a second periodic elastic distribution, the first and second periodic elastic distributions mutually converging at two positions and spaced apart therebetween, forming alternating annular regions of high amplitude and low amplitude formed by curved sections of the first and second periodic elastic distributions, wherein the core is positioned in a location coincident with an annular region of high amplitude.

2. The disposable absorbent article of claim 1, wherein the multiple distributions of elastics are disposed between the topsheet layer and the core.

3. The disposable absorbent article of claim 1, wherein the periodic elastic distributions each extend continuously from a section of low amplitude, across a section of high amplitude wherein said core is placed, to another section of low amplitude.

4. The disposable absorbent article of claim 1, wherein the core is situated between the first and the second curvilinear distribution of elastics.

5. The disposable absorbent article of claim 1, wherein the at least two curvilinear distributions of elastics are disposed about and proximate the periphery of the core and form a pocket or cup shape in the core.

6. The disposable absorbent article of claim 1, wherein the at least two curvilinear distributions of elastics are disposed about a periphery of the core.

7. The disposable absorbent article of claim 6, wherein the at least two curvilinear distributions of elastics form an annular elastic region along the periphery of the core.

8. The disposable absorbent article of claim 7, wherein the annular elastic region along the periphery of the core forms an O-ring seal about the core.

9. The disposable absorbent article of claim 6, wherein the at least two curvilinear distributions of elastics disposed about the periphery of the core form an upwardly biased elasticized pocket about the core.

10. The disposable absorbent article of claim 9, further comprising one or more central apertures into a space between the core and the topsheet layer and the intermediate nonwoven layer.

11. The disposable absorbent article of claim 1, further comprising an intermediate nonwoven layer disposed between the topsheet layer and the backsheet layer, wherein the multiple distributions of elastics are sandwiched between the topsheet layer and the intermediate nonwoven layer, and wherein the core is disposed between the intermediate nonwoven layer and the backsheet layer.

12. The disposable absorbent article of claim 11, wherein the at least two curvilinear distributions disposed of elastics are disposed about a periphery of the core and form an upwardly biased elasticized pocket about the topsheet layer and the intermediate nonwoven layer.

13. The disposable absorbent article of claim 12, further comprising one or more central apertures into a space between the core and the topsheet layer and the intermediate nonwoven layer.

14. The disposable absorbent article of claim 11, further comprising an acquisition distribution layer disposed between the core and the intermediate nonwoven layer.

15. A disposable absorbent article comprising:
a topsheet layer;
a backsheet layer;
multiple distributions of elastics disposed between the topsheet layer and the backsheet layer; and
a core disposed between the toposheet layer and the backsheet layer;
wherein the multiple distributions of elastics are disposed between the topsheet layer and the core, and include at least two curvilinear distributions of elastics, the at least two curvilinear distributions of elastics forming an annular elastic region and an upwardly biased elasticized pocket about the core.

16. The disposable absorbent article of claim 15, further comprising an intermediate nonwoven layer disposed between the topsheet layer and the backsheet layer, wherein the multiple distributions of elastics are sandwiched between the topsheet layer and the intermediate nonwoven layer, and wherein the core is disposed between the intermediate nonwoven layer and the backsheet layer.

17. The disposable absorbent article of claim 16, further comprising one or more central apertures into a space between the core and the topsheet layer and the intermediate nonwoven layer.

18. A method of making a disposable absorbent article, the method comprising:
conveying a first material sheet;
applying multiple distributions of elastics to the first material sheet, forming an elastic composite web;
applying a core to the elastic composite web;
applying a second material sheet to the elastic composite web including the core;
wherein applying the multiple distributions of elastics includes periodically varying a lateral position of the distributions of elastics relative to the machine direction of the elastic composite web to establish two curvilinear patterns on the elastic composite web, whereby the two curvilinear patterns include alternating sections of low amplitude and high amplitude; and
wherein applying the core on the elastic composite web includes placing the core in locations of the elastic composite web corresponding to a section of high amplitude, whereby said elastic distributions extend continuously from a section of low amplitude, across a section of high amplitude wherein said core is placed, to another section of low amplitude.

19. The method of claim 18, wherein the second material sheet is a topsheet layer of the disposable absorbent article and the first material sheet is a backsheet layer of the disposable absorbent article.

20. The method of claim 18, wherein applying the multiple distributions of elastics to the first material sheet forming the elastic composite web includes forming an upwardly biased elasticized pocket about the core with the at least two curvilinear distributions of elastics disposed about a periphery of the core.

21. The method of claim 18, wherein the at least two curvilinear distributions of elastics form an annular elastic region along the periphery of the core.

22. The method of claim 21, wherein the annular elastic region along the periphery of the core forms an O-ring seal about the core.

23. The method of claim 18, further comprising, prior to applying the core, applying an intermediate nonwoven layer to the elastic composite web, wherein the multiple distributions of elastics are disposed between the intermediate nonwoven layer and the topsheet layer.

24. The method of claim 23, wherein applying the multiple distributions of elastics to the first material sheet forming the elastic composite web includes forming an upwardly biased elasticized pocket about the topsheet layer and the intermediate nonwoven layer with the at least two curvilinear distributions of elastics disposed about the periphery of the core.

* * * * *